(12) United States Patent
Xu et al.

(10) Patent No.: US 10,683,256 B2
(45) Date of Patent: Jun. 16, 2020

(54) PROCESS FOR PREPARING SUBSTITUTED BIPHENYLS

(71) Applicant: BASF SE, Ludwigshafen (DE)

(72) Inventors: Xiaoming Xu, Taizhou (CN); Chao Huang, Taizhou (CN); Timo Frassetto, Mannheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 16/326,940

(22) PCT Filed: Aug. 22, 2016

(86) PCT No.: PCT/CN2016/096260
§ 371 (c)(1),
(2) Date: Feb. 21, 2019

(87) PCT Pub. No.: WO2018/035685
PCT Pub. Date: Mar. 1, 2018

(65) Prior Publication Data
US 2019/0210954 A1    Jul. 11, 2019

(51) Int. Cl.
*C07C 201/12* (2006.01)
*C07C 205/12* (2006.01)
*C07B 37/04* (2006.01)
*C07F 9/6568* (2006.01)
*B01J 31/24* (2006.01)

(52) U.S. Cl.
CPC ............ *C07C 201/12* (2013.01); *C07B 37/04* (2013.01); *C07C 205/12* (2013.01); *C07F 9/65683* (2013.01); *B01J 31/2438* (2013.01); *B01J 2231/4211* (2013.01); *B01J 2531/824* (2013.01)

(58) Field of Classification Search
CPC ... C07C 209/68; C07C 233/66; C07C 231/12; C07C 233/15; C07C 211/52; C07F 9/5004; C07F 9/5407; C07F 9/5442; C07F 9/5022; C07B 37/04
See application file for complete search history.

(56) References Cited

U.S. PATENT DOCUMENTS

| | | | |
|---|---|---|---|
| 8,455,689 B2* | 6/2013 | Dockner | C07C 231/12 564/221 |
| 9,096,626 B2* | 8/2015 | Haddad | C07B 37/04 |
| 9,868,694 B2* | 1/2018 | Dockner | C07F 9/5004 |
| 2011/0105766 A1 | 5/2011 | Smidt et al. | |
| 2016/0280635 A1 | 9/2016 | Dockner et al. | |
| 2017/0362263 A1* | 12/2017 | Lipshutz | C07F 9/657163 |

FOREIGN PATENT DOCUMENTS

| | | |
|---|---|---|
| WO | 09156359 A2 | 12/2009 |
| WO | 15011032 A1 | 1/2015 |
| WO | 17025377 A1 | 2/2017 |

OTHER PUBLICATIONS

Zhao et al., "An Efficient Method for Sterically Demanding Suzuki-Miyaura Coupling Reactions," Chem. Eur. J., vol. 19, (2013), pp. 2261-2264.
International Search Report, issued in PCT/CN2016/096260, dated Mar. 21, 2017.

* cited by examiner

*Primary Examiner* — Jafar F Parsa
(74) *Attorney, Agent, or Firm* — Marshall, Gerstein & Borun LLP

(57) ABSTRACT

The present invention relates to a process for preparing substituted biphenyls via Suzuki coupling using specific phosphorus ligands and a solvent mixture containing water, a non-polar organic solvent and a polar aprotic co-solvent.

20 Claims, No Drawings

PROCESS FOR PREPARING SUBSTITUTED BIPHENYLS

This application is a National Stage application of International Application No. PCT/CN2016/096260, filed Aug. 22, 2016.

The present invention relates to a process for preparing substituted biphenyls via Suzuki coupling using specific phosphorus ligands and a solvent mixture containing water, a non-polar organic solvent and a polar aprotic co-solvent.

Functionalized biphenyl compounds are of great interest especially as pharmaceuticals and pesticides, and as precursors of such active ingredients. For instance, 2-nitro and 2-aminobiphenyls are important precursors for aryl- and heteroarylcarboxamides which find use as fungicides, and for which boscalid, fluxapyroxad, bixafen or pyraziflumid are prominent representatives. For their synthesis, a series of organometallic methods is available, which offer efficient access to a multitude of biphenyl derivatives. The most frequently applied is the Suzuki coupling.

The Suzuki coupling (also called Suzuki-Miyaura coupling or Suzuki reaction or Suzuki-Miyaura reaction) is a cross coupling reaction in which an organoboron compound is reacted with an organic halogenide or sulfonate in the presence of a transition metal catalyst, mostly a Pd or Ni catalyst, and in general also of a base.

WO 2009/156359 relates to a process for preparing nitro- or aminobiphenyls by Suzuki coupling in the presence of a base and a palladium catalyst containing a bidentate phosphorus ligand derived from dppp, but containing substituents in the alkylene bridge. In the example, the coupling reaction in carried out in a mixture of water and THF as solvent in the presence of NaOH as base.

WO 2015/011032 relates to a process for preparing chlorinated biphenylanilines or anilides by Suzuki coupling using a palladium catalyst containing an optionally substituted di-tert-butylphenyl phosphine or a salt thereof as ligand. This catalyst is said to avoid the undesired formation of triphenyl compounds. In the examples the coupling reaction in carried out in a mixture of water and 1-butanol as solvent in the presence of potassium carbonate as base.

Principally, the known processes for preparing nitro- or aminobiphenyls via Suzuki coupling work well, at least on a laboratory scale. However, there is still room for improvement, especially with respect to an application in large-scale industrial processes. For instance, the amount of required Pd in the catalyst is still rather high. The solvents usually applied in industrial processes, mostly water and a water-miscible solvent, are difficult to remove. In order to keep the process economic, the obtained biphenyl often contains water, which can be disadvantageous in the subsequent reaction steps.

It was thus an object of the present invention to provide a process for producing nitro-, (substituted) amino-, amido- or imino-substituted biphenyls via Suzuki coupling which avoids some of the drawbacks of the prior art processes, especially when these are applied on a large scale. Especially it was the object of the present invention to provide a process for producing nitro-, (substituted) amino-, amido- or imino-substituted biphenyls via Suzuki coupling which requires distinctly lower amounts of palladium, suppresses homocoupling and is well-suited for large-scale applications.

The object is solved by the use of a specific ligand for the palladium catalyst, and by the use of a specific solvent mixture containing water, a non-polar organic solvent and a polar-aprotic organic solvent.

The invention thus relates to a process for preparing substituted biphenyls of the formula I

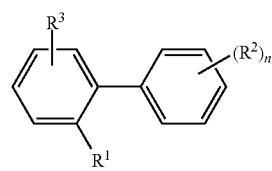

in which the substituents are each defined as follows:

$R^1$ is nitro, amino, $C_1$-$C_4$-alkylamino, —N(H)PG, —NH—CO—R', —N=CR'R" or a moiety of the formula $Q^1$, $Q^2$ or $Q^3$

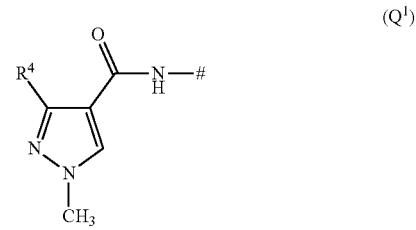

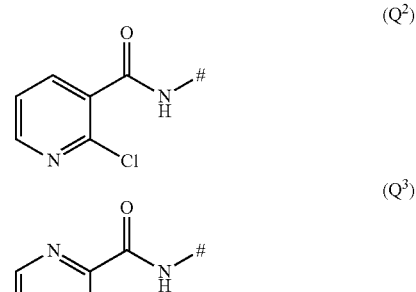

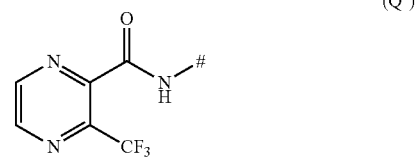

with

PG being a protective group;

R' and R" being independently of each other and independently of each occurrence $C_1$-$C_4$-alkyl or phenyl, where phenyl may carry 1, 2 or 3 substituents selected from halogen, $C_1$-$C_4$-alkyl, $C_1$-$C_4$-haloalkyl, $C_1$-$C_4$-alkoxy and $C_1$-$C_4$-haloalkoxy;

$R^4$ being methyl, optionally substituted by 1, 2 or 3 fluorine atoms, and being the attachment point to the remainder of the molecule (i.e. to the biphenyl moiety);

$R^2$ is cyano, nitro, halogen, $C_1$-$C_4$-alkyl, $C_1$-$C_4$-haloalkyl, $C_1$-$C_4$-alkoxy, $C_1$-$C_4$-haloalkoxy, $C_3$-$C_{10}$-cycloalkyl which may carry 1, 2, 3 or 4 $C_1$-$C_4$-alkyl substituents; $C_3$-$C_{10}$-halocycloalkyl, $C_1$-$C_6$-alkoxy, $C_1$-$C_6$-haloalkoxy, $C_1$-$C_6$-alkylcarbonyl; $C_1$-$C_6$-haloalkylcarbonyl; $C_1$-$C_6$-alkoxycarbonyl; $C_1$-$C_6$-haloalkoxycarbonyl; aryl; aryl-$C_1$-$C_4$-alkyl; arylcarbonyl; aryl-$C_1$-$C_4$-alkylcarbonyl; aryloxycarbonyl; aryl-$C_1$-$C_4$-alkoxycarbonyl, wherein aryl in the six last-mentioned radicals may carry 1, 2, 3 or 4 substituents selected from halogen, cyano, nitro, $C_1$-$C_4$-alkyl, $C_1$-$C_4$-haloalkyl, $C_1$-$C_4$-alkoxy and $C_1$-$C_4$-haloalkoxy; aminocarbonyl, $C_1$-$C_4$-alkylaminocarbonyl, and di-($C_1$-$C_4$-alkyl)-aminocarbonyl;

n is 0, 1, 2 or 3, where, in case that n=2 or 3, the $R^2$ radicals may have identical or different definitions; and $R^3$ is hydrogen, cyano, halogen, $C_1$-$C_4$-alkyl, $C_1$-$C_4$-haloalkyl or $C_1$-$C_4$-alkoxy;

which comprises reacting a halobenzene of the formula II

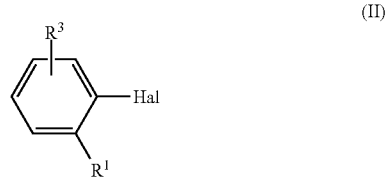

in which Hal is chlorine or bromine and $R^1$ and $R^3$ are each as defined above, in the presence of a base and of a palladium catalyst which comprises a palladium source and a phosphorus ligand of the formula III

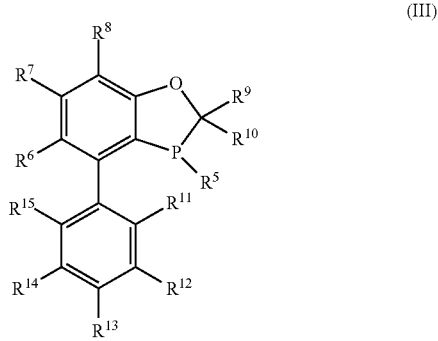

in which $R^5$ is $C_1$-$C_6$-alkyl, trifluoromethyl, $C_6$-$C_{10}$-aryl or 5- to 10-membered heteroaryl containing 1, 2, 3 or 4 heteroatoms selected from N and O as ring members;

$R^6$, $R^7$, $R^8$ are each independently selected from the group consisting of hydrogen, trifluoromethyl, $C_1$-$C_6$-alkyl, $C_1$-$C_6$-alkoxy, $C_3$-$C_{10}$-cycloalkyl, 5- to 11-membered saturated, partially unsaturated or maximally unsaturated heterocyclyl containing 1, 2, 3 or 4 heteroatoms or heteroatom groups selected from N, O, NO and $SO_2$ as ring members, $C_6$-$C_{10}$-aryl and $NR^{16}R^{17}$, wherein the above $C_3$-$C_{10}$-cycloalkyl, 5- to 11-membered heterocyclyl and $C_6$-$C_{10}$-aryl groups are optionally substituted with 1, 2 or 3 substituents independently selected from the group consisting of $C_1$-$C_6$-alkyl, $C_1$-$C_6$-alkoxy and trifluoromethyl; or $R^6$ and $R^7$, or $R^7$ and $R^8$, together with the carbon atoms they are bound to, form a 5- or 6-membered partially unsaturated or maximally unsaturated carbocyclic or heterocyclic ring, where the heterocyclic ring contains 1, 2, 3 or 4 heteroatoms or heteroatom groups selected from N, O, NO and $SO_2$ as ring members; where the carbocyclic or heterocyclic ring may carry one or more substituents selected from trifluoromethyl, $C_1$-$C_6$-alkyl, $C_1$-$C_6$-alkoxy, $C_3$-$C_{10}$-cycloalkyl, 5- to 11-membered saturated, partially unsaturated or maximally unsaturated heterocyclyl containing 1, 2, 3 or 4 heteroatoms or heteroatom groups selected from N, O, NO and $SO_2$ as ring members, $C_6$-$C_{10}$-aryl and $NR^{16}R^{17}$, wherein the above $C_3$-$C_{10}$-cycloalkyl, 5- to 11-membered heterocyclyl and $C_6$-$C_{10}$-aryl groups are optionally substituted with 1, 2 or 3 substituents independently selected from the group consisting of $C_1$-$C_6$-alkyl, $C_1$-$C_6$-alkoxy and trifluoromethyl;

$R^9$, $R^{10}$ are each independently selected from the group consisting of hydrogen, $C_1$-$C_6$-alkyl, $C_3$-$C_6$-cycloalkyl, 3- to 6-membered saturated, partially unsaturated or maximally unsaturated heterocyclyl containing 1, 2, 3 or 4 heteroatoms or heteroatom groups selected from N, O, NO and $SO_2$ as ring members, $C_6$-$C_{10}$-aryl and $Si(R^{16})_3$, wherein the above $C_3$-$C_6$-cycloalkyl, 3- to 6-membered heterocyclyl and $C_6$-$C_{10}$-aryl groups are optionally substituted with 1, 2 or 3 substituents independently selected from the group consisting of $C_1$-$C_6$-alkyl, $C_1$-$C_6$-alkoxy and trifluoromethyl;

$R^{11}$, $R^{12}$, $R^{13}$, $R^{14}$, $R^{15}$ are each independently selected from the group consisting of hydrogen, halogen, trifluoromethyl, $C_1$-$C_6$-alkoxy, $C_3$-$C_{10}$-cycloalkyl, 5- to 11-membered saturated, partially unsaturated or maximally unsaturated heterocyclyl containing 1, 2, 3 or 4 heteroatoms or heteroatom groups selected from N, O, NO and $SO_2$ as ring members, $C_6$-$C_{10}$-aryl, $NR^{16}R^{17}$, $-Si(R^{16})_3$ and $-SR^{16}$, wherein the above $C_3$-$C_{10}$-cycloalkyl, 5- to 11-membered heterocyclyl and $C_6$-$C_{10}$-aryl groups are optionally substituted with 1, 2 or 3 substituents independently selected from the group consisting of $C_1$-$C_6$-alkyl, $C_1$-$C_6$-alkoxy and trifluoromethyl;

or any two adjacent instances of $R^{11}$, $R^{12}$, $R^{13}$, $R^{14}$, $R^{15}$, together with the carbon atoms to which they are bound, form a five- or six-membered partially unsaturated or maximally unsaturated carbocyclic or heterocyclic ring, where the heterocyclic ring contains 1, 2, 3 or 4 heteroatoms or heteroatom groups selected from N, O, NO and $SO_2$ as ring members; where the carbocyclic or heterocyclic ring may carry one or more substituents selected from trifluoromethyl, $C_1$-$C_6$-alkyl, $C_1$-$C_6$-alkoxy, $C_3$-$C_{10}$-cycloalkyl, $C_6$-$C_{10}$-aryl, 5- to 11-membered saturated, partially unsaturated or maximally unsaturated heterocyclyl containing 1, 2, 3 or 4 heteroatoms or heteroatom groups selected from N, O, NO and $SO_2$ as ring members, and $NR^{16}R^{17}$, wherein the above $C_3$-$C_{10}$-cycloalkyl, 5- to 11-membered heterocyclyl and $C_6$-$C_{10}$-aryl groups are optionally substituted with 1, 2 or 3 substituents independently selected from the group consisting of $C_1$-$C_6$-alkyl, $C_1$-$C_6$-alkoxy and trifluoromethyl;

$R^{16}$, $R^{17}$ are each independently selected from the group consisting of hydrogen, trifluoromethyl, $C_1$-$C_6$-alkyl, $C_3$-$C_{10}$-cycloalkyl, saturated, partially unsaturated or maximally unsaturated 5- to 11-membered heterocyclyl containing 1, 2, 3 or 4 heteroatoms or heteroatom groups selected from N, O, NO and $SO_2$ as ring members, $C_6$-$C_{10}$-aryl, wherein the above $C_3$-$C_{10}$-cycloalkyl, 5- to 11-membered heterocyclyl and $C_6$-$C_{10}$-aryl groups are optionally substituted with 1, 2 or 3 substituents independently selected from the group consisting of halogen, $C_1$-$C_6$-alkyl, $C_1$-$C_6$-alkoxy and trifluoromethyl;

in a solvent mixture of water, a non-polar organic solvent and a polar aprotic co-solvent, with an organoboron compound of the formula IV

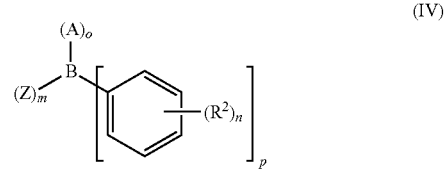

wherein $R^2$ and n are as defined above and the compound of formula IV is selected from the group consisting of
(i) boronic acids with o=0, m=2; p=1 and Z=hydroxyl groups,
or their trimers;
(ii) boronic acid derivates with o=0, m=2; p=1 and Z=halogen; $C_1$-$C_4$-alkyl, $C_1$-$C_6$-alkoxy, $C_6$-$C_{10}$-aryl or $C_6$-$C_{10}$-aryloxy;
(iii) borinic acids or borinic acid derivatives with o=0, m=1; p=2 and Z=hydroxy, halogen, $C_1$-$C_4$-alkyl, $C_1$-$C_6$-alkoxy, $C_6$-$C_{10}$-aryl or $C_6$-$C_{10}$-aryloxy;
(iv) mixed borinic acids or borinic acid derivatives with o=1, m=1; p=1, A=$C_1$-$C_4$-alkyl and Z=hydroxy, halogen, $C_1$-$C_4$-alkyl, $C_1$-$C_6$-alkoxy, $C_6$-$C_{10}$-aryl or $C_6$-$C_{10}$-aryloxy;
(v) cyclic boronic esters with o=0, m=2 and p=1, wherein the two Z groups form together a bridging group —O—$(CH_2)_q$—O—, wherein q is 2 or 3, so that the two Z groups, together with the boron atom to which they are attached, form a 5- or 6-membered ring, where the $CH_2$ groups are optionally substituted by one or two $C_1$-$C_4$-alkyl groups;
(vi) boronates with o=0, m=3, p=1 and Z=hydroxyl, halogen, $C_1$-$C_4$-alkyl, $C_1$-$C_6$-alkoxy, $C_6$-$C_{10}$-aryl or $C_6$-$C_{10}$-aryloxy, and accompanied by a cation which compensates the negative charge of the boronate anion;
(vii) triarylboranes with o=0, m=0 and p=3;
(viii) tetraarylborates with o=0, m=0 and p=4, and accompanied by a cation which compensates the negative charge of the borate anion.

In the definition of the above compounds Ill, the term "any two adjacent instances of $R^{11}$, $R^{12}$, $R^{13}$, $R^{14}$, $R^{15}$, together with the carbon atoms to which they are bound, form a five- or six-membered partially unsaturated or maximally unsaturated carbocyclic or heterocyclic ring" means that $R^{11}$ and $R^{12}$, or $R^{12}$ and $R^{13}$, or $R^{13}$ and $R^{14}$, or $R^{14}$ and $R^{15}$, together with the carbon atoms to which they are bound, form a five- or six-membered partially unsaturated or maximally unsaturated carbocyclic or heterocyclic ring as defined above. The term also includes the possibility that two pairs of $R^{11}$, $R^{12}$, $R^{13}$, $R^{14}$, $R^{15}$, together with the carbon atoms to which they are bound, form a ring, e.g. $R^{11}$ and $R^{12}$, and simultaneously also $R^{13}$ and $R^{14}$ or $R^{14}$ and $R^{15}$; or $R^{12}$ and $R^{13}$ and simultaneously also $R^{14}$ and $R^{15}$, form a ring.

The organic moieties mentioned in the above definitions of the variables are—like the term halogen—collective terms for individual listings of the individual group members. The prefix $C_n$-$C_m$ indicates in each case the possible number of carbon atoms in the group.

The term halogen denotes in each case fluorine, bromine, chlorine or iodine, in particular fluorine, chlorine or bromine.

The term "alkyl" as used herein and in the alkyl moieties of alkoxy, alkylcarbonyl, alkoxycarbonyl and the like refers to saturated straight-chain or branched hydrocarbon radicals having 1 to 2 ("$C_1$-$C_2$-alkyl"), 1 to 3 ("$C_1$-$C_3$-alkyl"), 1 to 4 ("$C_1$-$C_4$-alkyl") or 1 to 6 ("$C_1$-$C_6$-alkyl") carbon atoms. $C_1$-$C_2$-Alkyl is methyl or ethyl. $C_1$-$C_3$-Alkyl is additionally propyl and isopropyl. $C_1$-$C_4$-Alkyl is additionally n-butyl, 1-methylpropyl (sec-butyl), 2-methylpropyl (isobutyl) or 1,1-dimethylethyl (tert-butyl). $C_1$-$C_6$-Alkyl is additionally also, for example, pentyl, 1-methylbutyl, 2-methylbutyl, 3-methylbutyl, 2,2-dimethylpropyl, 1-ethylpropyl, 1,1-dimethylpropyl, 1,2-dimethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, or 1-ethyl-2-methylpropyl.

The term "haloalkyl" as used herein, which is also expressed as "alkyl which is partially or fully halogenated", refers to straight-chain or branched alkyl groups having 1 to 2 ("$C_1$-$C_2$-haloalkyl"), 1 to 3 ("$C_1$-$C_3$-haloalkyl"), 1 to 4 ("$C_1$-$C_4$-haloalkyl") or 1 to 6 ("$C_1$-$C_6$-haloalkyl") carbon atoms (as mentioned above), where some or all of the hydrogen atoms in these groups are replaced by halogen atoms as mentioned above: in particular $C_1$-$C_2$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl. $C_1$-$C_3$-haloalkyl is additionally, for example, 1-fluoropropyl, 2-fluoropropyl, 3-fluoropropyl, 1,1-difluoropropyl, 2,2-difluoropropyl, 1,2-difluoropropyl, 3,3-difluoropropyl, 3,3,3-trifluoropropyl, heptafluoropropyl, 1,1,1-trifluoroprop-2-yl, 3-chloropropyl and the like. Examples for $C_1$-$C_4$-haloalkyl are, apart those mentioned for $C_1$-$C_3$-haloalkyl, 4-chlorobutyl and the like.

"Methyl which is substituted by 1, 2 or 3 fluorine atoms" is fluoromethyl, difluoromethyl or trifluoromethyl.

"$C_1$-$C_6$-hydroxyalkyl" is a $C_1$-$C_6$-alkyl group, as defined above, wherein one of the hydrogen atoms has been replaced by an OH group. Examples are hydroxymethyl, 1-hydroxyethyl, 2-hydroxyethyl, 1-hydroxyprop-1-yl, 1-hydroxyprop-2-yl, 2-hydroxyprop-1-yl, 2-hydroxyprop-2-yl or 3-hydroxyprop-1-yl, 1-hydroxybut-1-yl, 1-hydroxybut-2-yl, 1-hydroxybut-3-yl, 2-hydroxybut-1-yl, 2-hydroxybut-2-yl, 2-hydroxybut-3-yl, 3-hydroxybut-1-yl, 4-hydroxybut-1-yl, 1-hydroxy-2-methyl-propy-1-yl, 2-hydroxy-2-methyl-propy-1-yl, 3-hydroxy-2-methyl-propy-1-yl, 2-(hydroxymethyl)-2-methyl-eth-1-yl, 1-hydroxypentyl, 2-hydroxypentyl, 3-hydroxypentyl, 4-hydroxypentyl, 5-hydroxypentyl, 1-hydroxyhexyl, 2-hydroxyhexyl, 3-hydroxyhexyl, 4-hydroxyhexyl, 5-hydroxyhexyl, 6-hydroxyhexyl, and the structure isomers thereof. If the hydroxyalkyl group is bound to a nitrogen or oxygen atom, the hydroxyl group is preferably not bound to that carbon atom of the alkyl group which is attached to the nitrogen or oxygen atom.

The term "cycloalkyl" as used herein refers to mono- or bicyclic saturated hydrocarbon radicals having 3 to 10 ("$C_3$-$C_{10}$-cycloalkyl"), 3 to 8 ("$C_3$-$C_8$-cycloalkyl"), in particular 3 to 6 ("$C_3$-$C_6$-cycloalkyl") or 3 to 5 ("$C_3$-$C_5$-cycloalkyl") or 3 to 4 ("$C_3$-$C_4$-cycloalkyl") carbon atoms. Examples of monocyclic radicals having 3 to 4 carbon atoms are cyclopropyl and cyclobutyl. Examples of monocyclic radicals having 3 to 5 carbon atoms are cyclopropyl, cyclobutyl and cyclopentyl. Examples of monocyclic radicals having 3 to 6 carbon atoms are cyclopropyl, cyclobutyl, cyclopentyl and cyclohexyl. Examples of monocyclic radicals having 3 to 8 carbon atoms are cyclopropyl, cyclobutyl, cyclopentyl, cyclohexyl, cycloheptyl and cyclooctyl. Examples of monocyclic radicals having 3 to 10 carbon atoms are cyclopropyl, cyclobutyl, cyclopentyl, cyclohexyl, cycloheptyl, cyclooctyl, cyclononyl and cyclodecyl. The bicyclic radicals can be condensed or bridged rings. Examples of bicyclic condensed radicals having 6 to 10 carbon atoms comprise bicyclo[3.1.0]hexyl, bicyclo[3.2.0] heptyl, bicyclo[3.3.0]octyl (1,2,3,3a,4,5,6,6a-octahydropentalenyl), bicyclo[4.2.0]octyl, bicyclo[4.3.0]nonyl (2,3,3a,4, 5,6,7,7a-octahydro-1H-indene), bicyclo[4.4.0]decyl (decalinyl) and the like. Examples of bridged bicyclic condensed radicals having 7 to 10 carbon atoms comprise bicyclo[2.2.1]heptyl, bicyclo[3.1.1]heptyl, bicyclo[2.2.2]octyl, bicyclo[3.2.1]octyl and the like. Preferably, the term cycloalkyl denotes a monocyclic saturated hydrocarbon radical.

The term "halocycloalkyl" as used herein, which is also expressed as "cycloalkyl which is partially or fully halogenated", refers to mono- or bicyclic saturated hydrocarbon groups having 3 to 10 ("$C_3$-$C_{10}$-halocycloalkyl") or 3 to 8 ("$C_3$-$C_8$-halocycloalkyl") or preferably 3 to 6 ("$C_3$-$C_6$-halocycloalkyl") or 3 to 5 ("$C_3$-$C_5$-halocycloalkyl") or 3 to 4 ("$C_3$-$C_4$-halocycloalkyl") carbon ring members (as mentioned above) in which some or all of the hydrogen atoms are replaced by halogen atoms as mentioned above, in particular fluorine, chlorine and bromine.

"Alkoxy" is an alkyl group attached via an oxygen atom. The term "$C_1$-$C_2$-alkoxy" is a $C_1$-$C_2$-alkyl group, as defined above, attached via an oxygen atom. The term "$C_1$-$C_3$-alkoxy" is a $C_1$-$C_3$-alkyl group, as defined above, attached via an oxygen atom. The term "$C_1$-$C_4$-alkoxy" is a $C_1$-$C_4$-alkyl group, as defined above, attached via an oxygen atom. The term "$C_1$-$C_6$-alkoxy" is a $C_1$-$C_6$-alkyl group, as defined above, attached via an oxygen atom. $C_1$-$C_2$-Alkoxy is methoxy or ethoxy. $C_1$-$C_3$-Alkoxy is additionally, for example, n-propoxy and 1-methylethoxy (isopropoxy). $C_1$-$C_4$-Alkoxy is additionally, for example, butoxy, 1-methylpropoxy (sec-butoxy), 2-methylpropoxy (isobutoxy) or 1,1-dimethylethoxy (tert-butoxy). $C_1$-$C_6$-Alkoxy is additionally, for example, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy.

"Haloalkoxy" is a haloalkyl group attached via an oxygen atom. The term "$C_1$-$C_2$-haloalkoxy" is a $C_1$-$C_2$-haloalkyl group, as defined above, attached via an oxygen atom. The term "$C_1$-$C_3$-haloalkoxy" is a $C_1$-$C_3$-haloalkyl group, as defined above, attached via an oxygen atom. The term "$C_1$-$C_4$-haloalkoxy" is a $C_1$-$C_4$-haloalkyl group, as defined above, attached via an oxygen atom. The term "$C_1$-$C_6$-haloalkoxy" is a $C_1$-$C_6$-haloalkyl group, as defined above, attached via an oxygen atom. $C_1$-$C_2$-Haloalkoxy is, for example, $OCH_2F$, $OCHF_2$, $OCF_3$, $OCH_2Cl$, $OCHCl_2$, $OCCl_3$, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy or $OC_2F_5$. $C_1$-$C_3$-Haloalkoxy is additionally, for example, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, $OCH_2$—$C_2F_5$, $OCF_2$—$C_2F_5$, 1-($CH_2F$)-2-fluoroethoxy, 1-($CH_2Cl$)-2-chloroethoxy or 1-($CH_2Br$)-2-bromoethoxy. $C_1$-$C_4$-Haloalkoxy is additionally, for example, 4-fluorobutoxy, 4-chlorobutoxy, 4-bromobutoxy or nonafluorobutoxy. $C_1$-$C_6$-Haloalkoxy is additionally, for example, 5-fluoropentoxy, 5-chloropentoxy, 5-brompentoxy, 5-iodopentoxy, undecafluoropentoxy, 6-fluorohexoxy, 6-chlorohexoxy, 6-bromhexoxy, 6-iodhexoxy or dodecafluorohexoxy.

The substituent "oxo" replaces a $CH_2$ group by a $C(=O)$ group.

The term "alkylcarbonyl" is a $C_1$-$C_6$-alkyl ("$C_1$-$C_6$-alkylcarbonyl"), preferably a $C_1$-$C_4$-alkyl ("$C_1$-$C_4$-alkylcarbonyl") group, as defined above, attached via a carbonyl [$C(=O)$] group. Examples are acetyl (methylcarbonyl), propionyl (ethylcarbonyl), propylcarbonyl, isopropylcarbonyl, n-butylcarbonyl and the like.

The term "haloalkylcarbonyl" is a $C_1$-$C_6$-haloalkyl ("$C_1$-$C_6$-haloalkylcarbonyl"), preferably a $C_1$-$C_4$-haloalkyl ("$C_1$-$C_4$-haloalkylcarbonyl") group, as defined above, attached via a carbonyl [$C(=O)$] group. Examples are trifluoromethylcarbonyl, 2,2,2-trifluoroethylcarbonyl and the like.

The term "alkoxycarbonyl" is a $C_1$-$C_6$-alkoxy ("$C_1$-$C_6$-alkoxycarbonyl"), preferably a $C_1$-$C_4$-alkoxy ("$C_1$-$C_4$-alkoxycarbonyl") group, as defined above, attached via a carbonyl [$C(=O)$] group. Examples are methoxycarbonyl, ethoxycarbonyl, propoxycarbonyl, isopropoxycarbonyl, n-butoxycarbonyl and the like.

The term "haloalkoxycarbonyl" is a $C_1$-$C_6$-haloalkoxy ("$C_1$-$C_6$-haloalkoxycarbonyl"), preferably a $C_1$-$C_4$-haloalkoxy ("$C_1$-$C_4$-haloalkoxycarbonyl") group, as defined above, attached via a carbonyl [$C(=O)$] group. Examples are trifluoromethoxycarbonyl, 2,2,2-trifluoroethoxycarbonyl and the like.

"Amino" is $NH_2$.

The term "$C_1$-$C_4$-alkylamino" is a group —$N(H)C_1$-$C_4$-alkyl. Examples are methylamino, ethylamino, propylamino, isopropylamino, butylamino and the like.

The term "di-($C_1$-$C_4$-alkyl)amino" is a group —$N(C_1$-$C_4$-alkyl)$_2$. Examples are dimethylamino, diethylamino, ethylmethylamino, dipropylamino, diisopropylamino, methylpropylamino, methylisopropylamino, ethylpropylamino, ethylisopropylamino, dibutylamino and the like.

The term "aminocarbonyl" is a group —$C(=O)$—$NH_2$.

The term "$C_1$-$C_4$-alkylaminocarbonyl" is a group —$C(=O)$—$N(H)C_1$-$C_4$-alkyl. Examples are methylaminocarbonyl, ethylaminocarbonyl, propylaminocarbonyl, isopropylaminocarbonyl, butylaminocarbonyl and the like.

The term "di-($C_1$-$C_4$-alkyl)aminocarbonyl" is a group —$C(=O)$—$N(C_1$-$C_4$-alkyl)$_2$. Examples are dimethylaminocarbonyl, diethylaminocarbonyl, ethylmethylaminocarbonyl, dipropylaminocarbonyl, diisopropylaminocarbonyl, methylpropylaminocarbonyl, methylisopropylaminocarbonyl, ethylpropylaminocarbonyl, ethylisopropylaminocarbonyl, dibutylaminocarbonyl and the like.

If the term "aryl" as used herein and in the aryl moieties of aryloxy, aryl-$C_1$-$C_4$-alkyl, arylcarbonyl and the like is used without prefix ($C_n$-$C_m$), it indicates an aryl group with 6 to 30, in particular 6 to 14, specifically 6 to 10 carbon atoms as ring members. Aryl is a mono-, bi- or polycyclic carbocyclic (i.e. without heteroatoms as ring members) aromatic radical. One example for a monocyclic aromatic radical is phenyl. In bicyclic aryl rings two aromatic rings are condensed, i.e. they share two vicinal C atoms as ring members. One example for a bicyclic aromatic radical is naphthyl. In polycyclic aryl rings, three or more rings are condensed. Examples for polycyclic aryl radicals are phenanthrenyl, anthracenyl, tetracenyl, 1H-benzo[a]phenalenyl, pyrenyl and the like.

"$C_6$-$C_{10}$-Aryl" is phenyl or naphthyl.

"Aryloxy" is aryl, as defined above, bound via an oxygen atom to the remainder of the molecule.

"$C_6$-$C_{10}$-Aryloxy" is phenoxy or naphthyloxy.

"Arylcarbonyl" is aryl, as defined above, bound via a carbonyl group [$C(=O)$] to the remainder of the molecule.

"$C_6$-$C_{10}$-Arylcarbonyl" is phenylcarbonyl (benzoyl) or naphthylcarbonyl.

"Aryl-$C_1$-$C_4$-alkyl" is aryl, as defined above, bound via a $C_1$-$C_4$-alkyl group to the remainder of the molecule.

"$C_6$-$C_{10}$-Aryl-$C_1$-$C_4$-alkyl" is for example benzyl, phenethyl or 1-phenylethyl.

"Aryl-$C_1$-$C_4$-alkylcarbonyl" is aryl, as defined above, bound via a $C_1$-$C_4$-alkyl-C(=O)— group to the remainder of the molecule.

"$C_6$-$C_{10}$-Aryl-$C_1$-$C_4$-alkylcarbonyl" is for example benzylcarbonyl, 2-phenylethylcarbonyl or 1-phenylethylcarbonyl.

"Aryloxycarbonyl" is aryl, as defined above, bound via an oxycarbonyl group [O—C(=O)] to the remainder of the molecule.

"$C_6$-$C_{10}$-Aryloxycarbonyl" is phenoxycarbonyl or naphthyloxycarbonyl.

"Aryl-$C_1$-$C_4$-alkoxycarbonyl" is aryl, as defined above, bound via a $C_1$-$C_4$-alkoxycarbonyl group [$C_1$-$C_4$-alkyl-O—C(=O)] to the remainder of the molecule.

"$C_6$-$C_{10}$-Aryl-$C_1$-$C_4$-alkoxycarbonyl" is for example benzyloxycarbonyl, 2-phenylethyloxycarbonyl or 1-phenylethyloxycarbonyl.

"5- to 11-membered heteroaryl containing 1, 2, 3 or 4 heteroatoms selected from N and O" is a monocyclic or a condensed system with 5, 6, 7, 8, 9, 10 or 11 ring members in which at least one of the rings is aromatic and which contains 1, 2, 3 or 4 heteroatoms selected from N and O.

Monocyclic heteroaryl is 5- or 6-membered. Examples for 5- or 6-membered monocyclic heteroaromatic rings containing 1, 2, 3 or 4 heteroatoms selected from N and O as ring members are 2-furyl, 3-furyl, 1-pyrrolyl, 2-pyrrolyl, 3-pyrrolyl, 1-pyrazolyl, 3-pyrazolyl, 4-pyrazolyl, 5-pyrazolyl, 1-imidazolyl, 2-imidazolyl, 4-imidazolyl, 5-imidazolyl, 2-oxazolyl, 4-oxazolyl, 5-oxazolyl, 3-isoxazolyl, 4-isoxazolyl, 5-isoxazolyl, 1,3,4-triazol-1-yl, 1,3,4-triazol-2-yl, 1,3,4-triazol-3-yl, 1,2,3-triazol-1-yl, 1,2,3-triazol-2-yl, 1,2,3-triazol-4-yl, 1,2,5-oxadiazol-3-yl, 1,2,3-oxadiazol-4-yl, 1,2,3-oxadiazol-5-yl, 1,3,4-oxadiazol-2-yl, 2-pyridinyl, 3-pyridinyl, 4-pyridinyl, 1-oxopyridin-2-yl, 1-oxopyridin-3-yl, 1-oxopyridin-4-yl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl, 1,2,4-triazin-5-yl, 1,2,3,4-tetrazin-1-yl, 1,2,3,4-tetrazin-2-yl, 1,2,3,4-tetrazin-5-yl and the like.

Bicyclic throughout aromatic heteroaryl is 9- or 10-membered. Examples are:

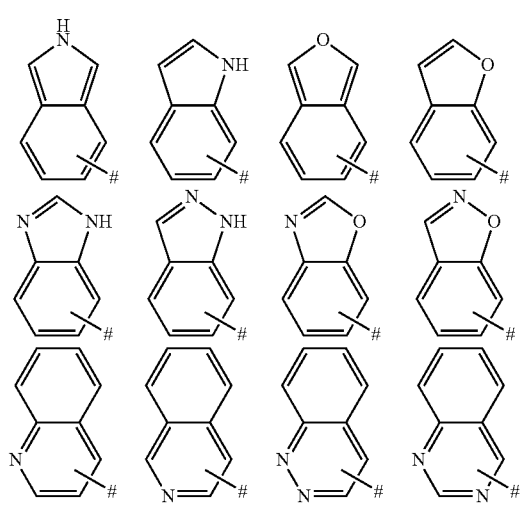

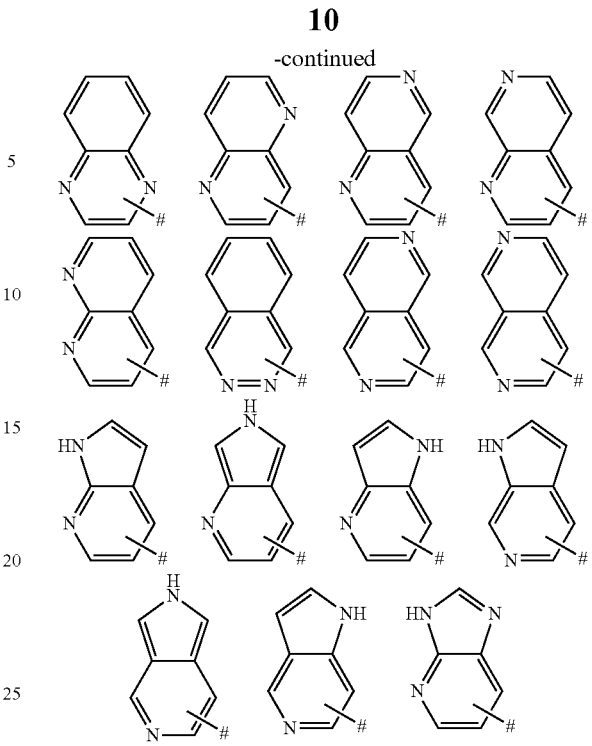

In the above structures # denotes the attachment point to the remainder of the molecule. The attachment point is not restricted to the ring on which this is shown, but can be on either of the two rings, and may be on a carbon or on a nitrogen ring atom. If the rings carry one or more substituents, these may be bound to carbon and/or to nitrogen ring atoms.

"5- to 11-membered saturated, partially unsaturated or maximally unsaturated heterocyclyl containing 1, 2, 3 or 4 heteroatoms or heteroatom groups selected from N, O, NO and $SO_2$ as ring members" [wherein "maximum unsaturated" includes also "aromatic"] as used herein denotes monocyclic or bicyclic radicals which may be saturated, partially unsaturated or maximum unsaturated (including aromatic) and contain 5, 6, 7, 8, 9, 10 or 11 ring members.

"3- to 6-membered saturated, partially unsaturated or maximally unsaturated heterocyclyl containing 1, 2, 3 or 4 heteroatoms or heteroatom groups selected from N, O, NO and $SO_2$ as ring members" [wherein "maximum unsaturated" includes also "aromatic"] as used herein denotes monocyclic radicals which may be saturated, partially unsaturated or maximum unsaturated (including aromatic) and contain 3, 4, 5 or 6 ring members.

Unsaturated rings contain at least one C—C and/or C—N and/or N—N double bond(s). Maximally unsaturated rings contain as many conjugated C—C and/or C—N and/or N—N double bonds as allowed by the ring size. Maximally unsaturated 5- or 6-membered heteromonocyclic rings are generally aromatic. Exceptions are maximally unsaturated 6-membered rings containing O and/or $SO_2$ as ring members, such as pyran, which are not aromatic. Partially unsaturated rings contain less than the maximum number of C—C and/or C—N and/or N—N double bond(s) allowed by the ring size. The heterocyclic ring may be attached to the remainder of the molecule via a carbon ring member or via a nitrogen ring member. As a matter of course, the heterocyclic ring contains at least one carbon ring atom. If the ring contains more than one O ring atom, these are not adjacent.

Examples of a 3-, 4-, 5-, 6-, 7- or 8-membered saturated heteromonocyclic ring include: Oxiran-2-yl, aziridin-1-yl, aziridin-2-yl, oxetan-2-yl, oxetan-3-yl, azetidin-1-yl, azetidin-2-yl, azetidin-3-yl, tetrahydrofuran-2-yl, tetrahydrofuran-3-yl, pyrrolidin-1-yl, pyrrolidin-2-yl, pyrrolidin-3-yl, pyrazolidin-1-yl, pyrazolidin-3-yl, pyrazolidin-4-yl, pyrazolidin-5-yl, imidazolidin-1-yl, imidazolidin-2-yl, imidazolidin-4-yl, oxazolidin-2-yl, oxazolidin-3-yl, oxazolidin-4-yl, oxazolidin-5-yl, isoxazolidin-2-yl, isoxazolidin-3-yl, isoxazolidin-4-yl, isoxazolidin-5-yl, 1,2,4-oxadiazolidin-2-yl, 1,2,4-oxadiazolidin-3-yl, 1,2,4-oxadiazolidin-4-yl, 1,2,4-oxadiazolidin-5-yl, 1,2,4-triazolidin-1-yl, 1,2,4-triazolidin-3-yl, 1,2,4-triazolidin-4-yl, 1,3,4-oxadiazolidin-2-yl, 1,3,4-oxadiazolidin-3-yl, 1,3,4-triazolidin-1-yl, 1,3,4-triazolidin-2-yl, 1,3,4-triazolidin-3-yl, tetrahydropyran-2-yl, tetrahydropyran-3-yl, tetrahydropyran-4-yl, 1,3-dioxan-2-yl, 1,3-dioxan-4-yl, 1,3-dioxan-5-yl, 1,4-dioxan-2-yl, piperidin-1-yl, piperidin-2-yl, piperidin-3-yl, piperidin-4-yl, hexahydropyridazin-1-yl, hexahydropyridazin-3-yl, hexahydropyridazin-4-yl, hexahydropyrimidin-1-yl, hexahydropyrimidin-2-yl, hexahydropyrimidin-4-yl, hexahydropyrimidin-5-yl, piperazin-1-yl, piperazin-2-yl, 1,3,5-hexahydrotriazin-1-yl, 1,3,5-hexahydrotriazin-2-yl, 1,2,4-hexahydrotriazin-1-yl, 1,2,4-hexahydrotriazin-2-yl, 1,2,4-hexahydrotriazin-3-yl, 1,2,4-hexahydrotriazin-4-yl, 1,2,4-hexahydrotriazin-5-yl, 1,2,4-hexahydrotriazin-6-yl, morpholin-2-yl, morpholin-3-yl, morpholin-4-yl, azepan-1-, -2-, -3- or -4-yl, oxepan-2-, -3-, -4- or -5-yl, hexahydro-1,3-diazepinyl, hexahydro-1,4-diazepinyl, hexahydro-1,3-oxazepinyl, hexahydro-1,4-oxazepinyl, hexahydro-1,3-dioxepinyl, hexahydro-1,4-dioxepinyl, oxocane, azocanyl, [1,3]diazocanyl, [1,4]diazocanyl, [1,5]diazocanyl, [1,5]oxazocanyl and the like.

Examples of a 3-, 4-, 5-, 6-, 7- or 8-membered partially unsaturated heteromonocyclic ring include: 2,3-dihydrofuran-2-yl, 2,3-dihydrofuran-3-yl, 2,4-dihydrofuran-2-yl, 2,4-dihydrofuran-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-, 3-, 4-, 5- or 6-di- or tetrahydropyridinyl, 3-di- or tetrahydropyridazinyl, 4-di- or tetrahydropyridazinyl, 2-di- or tetrahydropyrimidinyl, 4-di- or tetrahydropyrimidinyl, 5-di- or tetrahydropyrimidinyl, di- or tetrahydropyrazinyl, 1,3,5-di- or tetrahydrotriazin-2-yl, 1,2,4-di- or tetrahydrotriazin-3-yl, 2,3,4,5-tetrahydro[1H]azepin-1-, -2-, -3-, -4-, -5-, -6- or -7-yl, 3,4,5,6-tetrahydro[2H]azepin-2-, -3-, -4-, -5-, -6- or -7-yl, 2,3,4,7-tetrahydro[1H]azepin-1-, -2-, -3-, -4-, -5-, -6- or -7-yl, 2,3,6,7-tetrahydro[1H]azepin-1-, -2-, -3-, -4-, -5-, -6- or -7-yl, tetrahydrooxepinyl, such as 2,3,4,5-tetrahydro[1H]oxepin-2-, -3-, -4-, -5-, -6- or -7-yl, 2,3,4,7-tetrahydro[1H]oxepin-2-, -3-, -4-, -5-, -6- or -7-yl, 2,3,6,7-tetrahydro[1H]oxepin-2-, -3-, -4-, -5-, -6- or -7-yl, tetrahydro-1,3-diazepinyl, tetrahydro-1,4-diazepinyl, tetrahydro-1,3-oxazepinyl, tetrahydro-1,4-oxazepinyl, tetrahydro-1,3-dioxepinyl, tetrahydro-1,4-dioxepinyl, 1,2,3,4,5,6-hexahydroazocine, 2,3,4,5,6,7-hexahydroazocine, 1,2,3,4,5,8-hexahydroazocine, 1,2,3,4,7,8-hexahydroazocine, 1,2,3,4,5,6-hexahydro-[1,5]diazocine,1,2,3,4,7,8-hexahydro-[1,5]diazocine and the like.

Examples of a 3-, 4-, 5-, 6-, 7- or 8-membered maximally unsaturated (but not aromatic) heteromonocyclic ring are pyran-2-yl, pyran-3-yl, pyran-4-yl, 2H-oxazin-2-yl, 2H-oxazin-3-yl, 2H-oxazin-4-yl, 2H-oxazin-5-yl, 2H-oxazin-6-yl, 4H-oxazin-3-yl, 4H-oxazin-4-yl, 4H-oxazin-5-yl, 4H-oxazin-6-yl, 6H-oxazin-3-yl, 6H-oxazin-4-yl, 7H-oxazin-5-yl, 8H-oxazin-6-yl, 2H-1,3-oxazin-2-yl, 2H-1,3-oxazin-4-yl, 2H-1,3-oxazin-5-yl, 2H-1,3-oxazin-6-yl, 4H-1,3-oxazin-2-yl, 4H-1,3-oxazin-4-yl, 4H-1,3-oxazin-5-yl, 4H-1,3-oxazin-6-yl, 6H-1,3-oxazin-2-yl, 6H-1,3-oxazin-4-yl, 6H-1,3-oxazin-5-yl, 6H-1,3-oxazin-6-yl, 2H-1,4-oxazin-2-yl, 2H-1,4-oxazin-3-yl, 2H-1,4-oxazin-5-yl, 2H-1,4-oxazin-6-yl, 4H-1,4-oxazin-2-yl, 4H-1,4-oxazin-3-yl, 4H-1,4-oxazin-4-yl, 4H-1,4-oxazin-5-yl, 4H-1,4-oxazin-6-yl, 6H-1,4-oxazin-2-yl, 6H-1,4-oxazin-3-yl, 6H-1,4-oxazin-5-yl, 6H-1,4-oxazin-6-yl, 1,4-dioxine-2-yl, 1H-azepine, 1H-[1,3]-diazepine, 1H-[1,4]-diazepine, [1,3]diazocine, [1,5]diazocine, [1,5]diazocine and the like.

Heteroaromatic monocyclic rings are 5- or 6-membered. Examples for 5- or 6-membered monocyclic heteroaromatic rings containing 1, 2, 3 or 4 heteroatoms selected from N and O as ring members are given above under "heteroaryl".

Bicyclic heterocyclyl includes condensed (fused) ring systems, in which the two rings have two neighboring ring atoms in common, as well as spiro systems, in which the rings have only one ring atom in common, and bridged systems with at least three ring atoms in common.

Condensed Systems:

Examples for a 7-, 8-, 9-, 10- or 11-membered saturated heterobicyclic ring containing 1, 2, 3 or 4 heteroatoms or heteroatom groups selected from N, O, NO and $SO_2$, as ring members are:

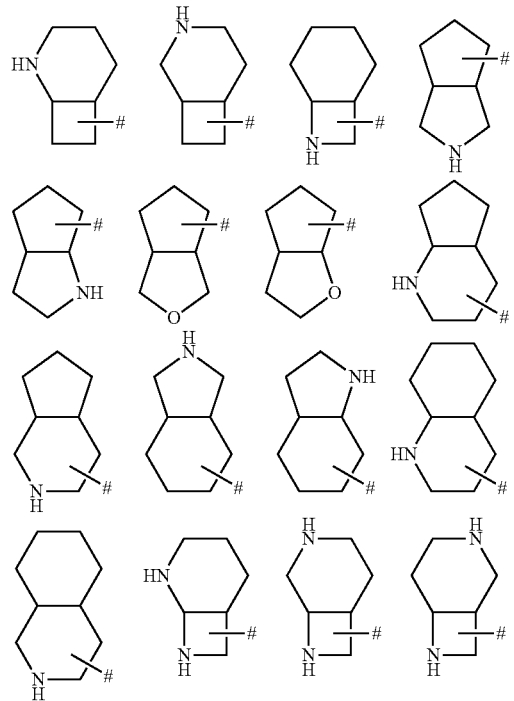

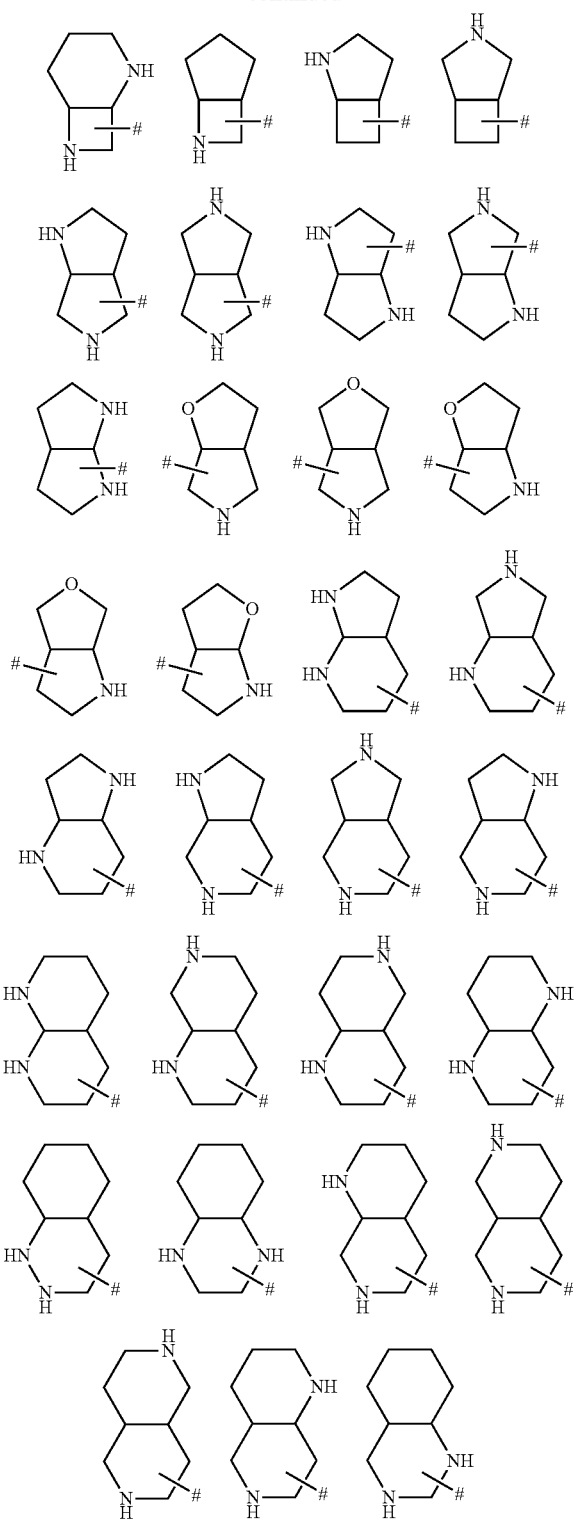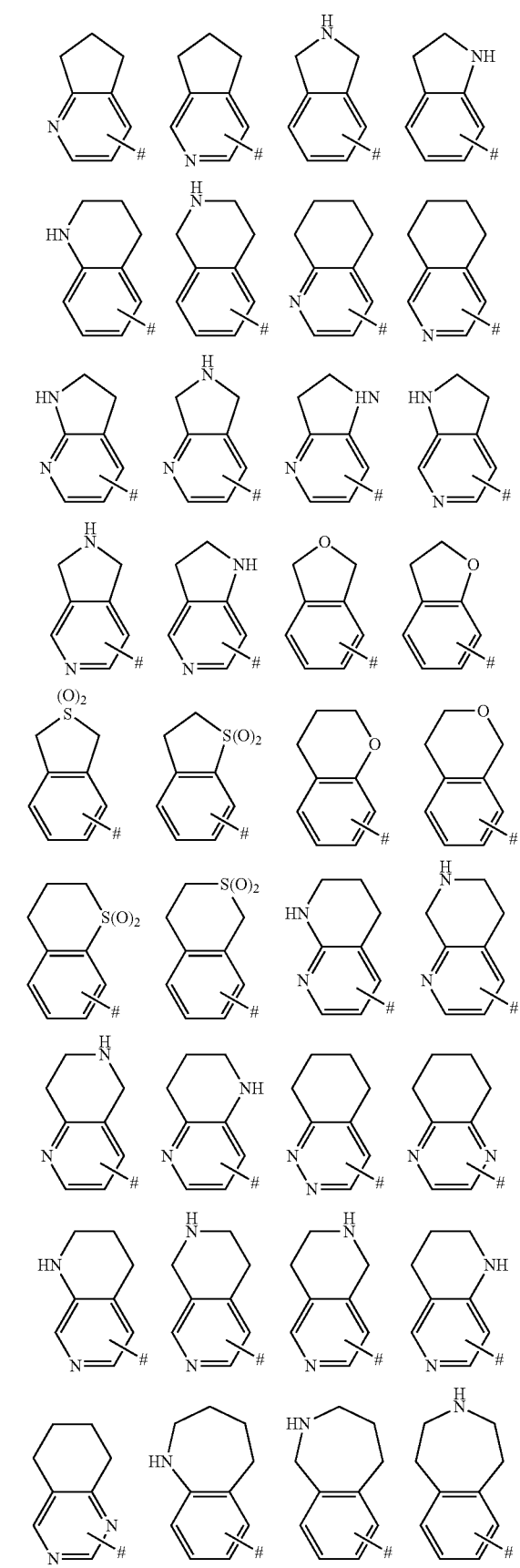
Examples for a 7-, 8-, 9-, 10- or 11-membered partially unsaturated heterobicyclic ring containing 1, 2, 3 or 4 heteroatoms or heteroatom groups selected from N, O, NO and $SO_2$, as ring members are:

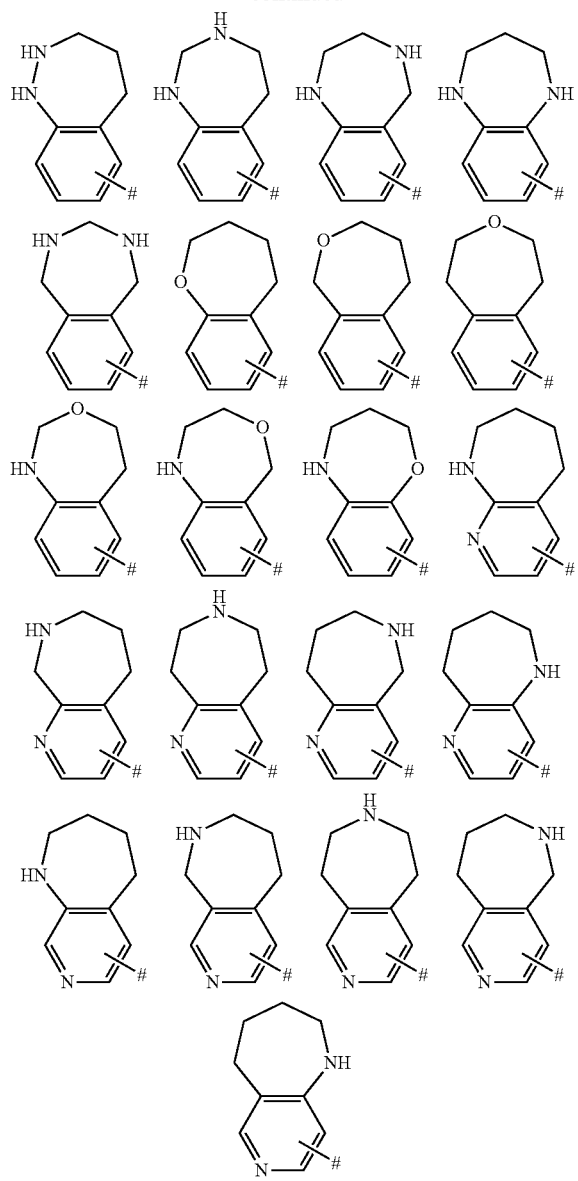

Examples for a 7-, 8-, 9-, 10- or 11-membered maximally unsaturated (but not throughout heteroaromatic) heterobicyclic ring containing 1, 2, 3 or 4 heteroatoms or heteroatom groups selected from N, O, NO and SO$_2$, as ring members are:

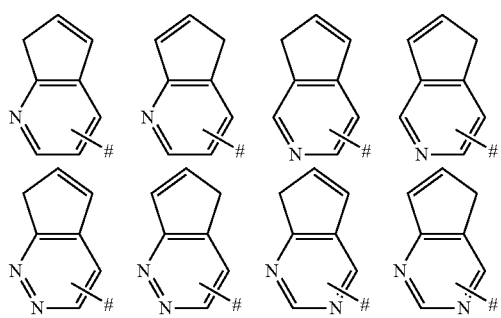

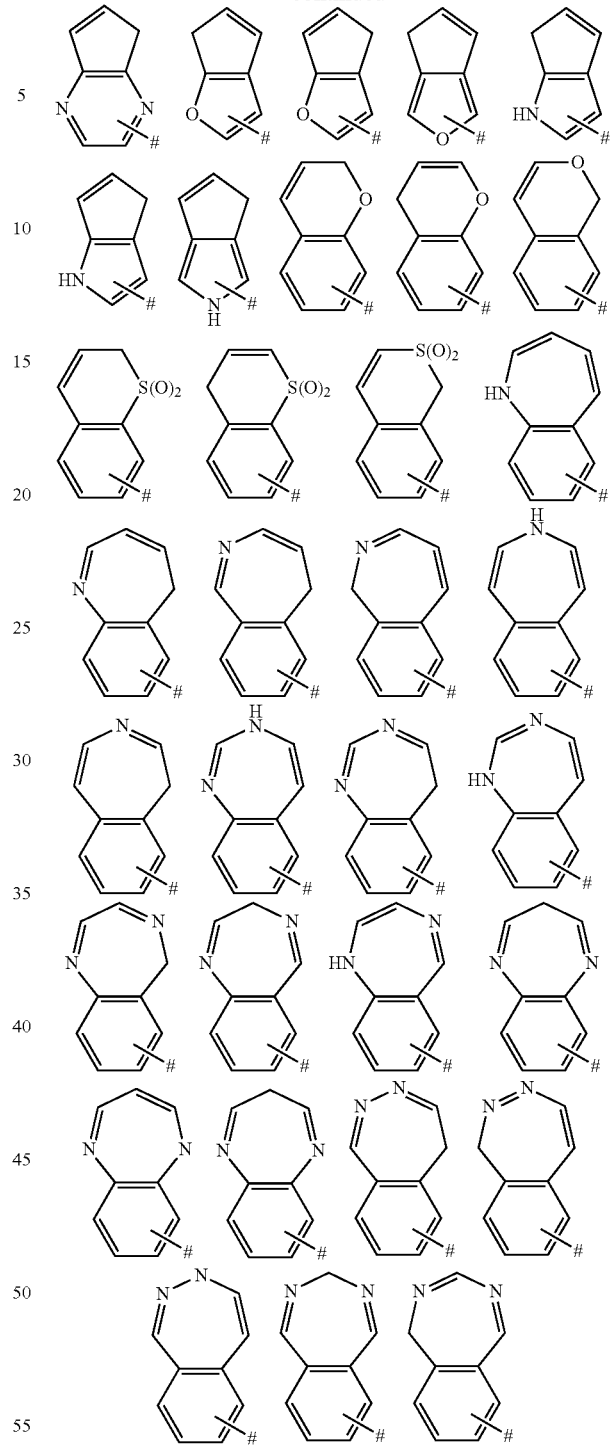

Examples for a 9- or 10-membered maximally unsaturated, throughout heteroaromatic heterobicyclic ring containing 1, 2, 3 or 4 heteroatoms or heteroatom groups selected from N, O, NO and SO$_2$, as ring members are given above under "heteroaryl".

Spiro Systems:

Examples for spiro-bound 7-, 8-, 9-, 10- or 11-membered heterobicyclic rings containing 1, 2 or 3 (or 4) heteroatoms or heteroatom groups selected from N, O, NO and SO$_2$, as ring members are

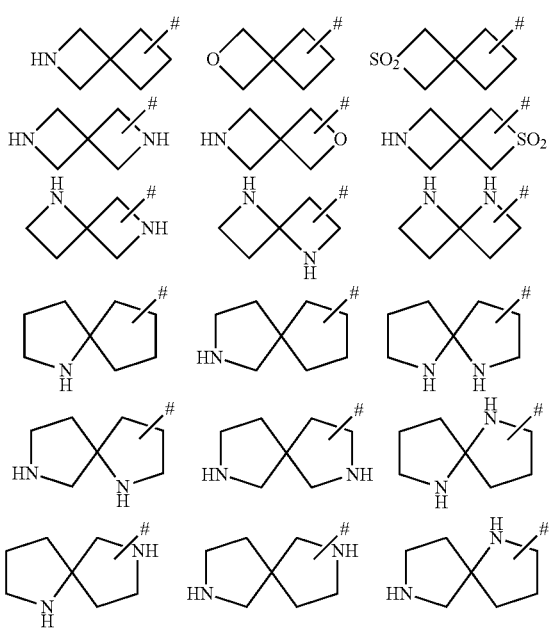

Bridged Systems:

Examples for bridged 7-, 8-, 9-, 10- or 11-membered heterobicyclic rings containing 1, 2 or 3 (or 4) heteroatoms or heteroatom groups selected from N, O, NO and $SO_2$, as ring members are

and the like.

In the above structures # denotes the attachment point to the remainder of the molecule. The attachment point is not restricted to the ring on which this is shown, but can be on either of the two rings, and may be on a carbon or on a nitrogen ring atom. If the rings carry one or more substituents, these may be bound to carbon and/or to nitrogen ring atoms.

The remarks made below regarding preferred embodiments of the process according to the invention, especially regarding preferred embodiments of the radicals of the different reactants and products (to be more precise preferred embodiments of the variables of the compounds of formulae I, II, III, IV and V, especially with respect to their substituents $R^1$, $R^2$, $R^3$, $R^4$, $R^5$, $R^6$, $R^8$, $R^9$, $R^{10}$, $R^{11}$, $R^{12}$, $R^{13}$, $R^{14}$, $R^{15}$, $R^{16}$, $R^{17}$, $R^x$, $R^y$, Q, $Q^1$, $Q^2$, $Q^3$, Z, m, n and p) and of the reaction conditions of the processes according to the invention, apply either taken alone or, more particularly, in any conceivable combination with one another.

The remarks to preferred embodiments or $R^1$ and $R^3$ apply both to formula I as well as to formula II, unless explicitly specified otherwise. The remarks to preferred embodiments of $R^2$ and n apply both to formula I as well as to formula IV, unless explicitly specified otherwise.

Suitable protecting groups PG and processes for introducing them are known to those skilled in the art. Suitable protective groups PG are for example $C_1$-$C_4$-alkylcarbonyl (e.g. acetyl), $C_1$-$C_4$-haloalkylcarbonyl (e.g. trifluoroacetyl), $C_3$-$C_4$-alkenylcarbonyl (e.g. allylcarbonyl), phenylcarbonyl, where phenyl may carry 1, 2 or 3 substituents selected from halogen, $C_1$-$C_4$-alkyl, $C_1$-$C_4$-haloalkyl, $C_1$-$C_4$-alkoxy and $C_1$-$C_4$-haloalkoxy; $C_1$-$C_4$-alkoxycarbonyl (e.g. ethoxycarbonyl, tert-butyloxycarbonyl (Boc)), $C_3$-$C_4$-alkenyloxycarbonyl, benzyloxycarbonyl (Cbz), $C_1$-$C_4$-alkylaminocarbonyl, di-($C_1$-$C_4$-alkyl)-aminocarbonyl, $C_1$-$C_4$-alkylsulfonyl, $C_1$-$C_4$-haloalkylsulfonyl or benzyl. Specifically, benzyl, $C_1$-$C_4$-alkoxycarbonyl (especially ethoxycarbonyl or Boc) or benzyloxycarbonyl (Cbz) are used.

The Schiff base —N=CR'R" generally also serves as a protective group for.

If $R^1$ contains halogen atoms bound to an aromatic or heteroaromatic ring (e.g. R' or R" are phenyl substituted by halogen, or PG is phenylcarbonyl, where phenyl carries one or more halogen substituents), this halogen atom is preferably chosen so that it does essentially not compete with Hal in compounds II, as otherwise the regioselectivity of the reaction might suffer.

In a particular embodiment, $R^4$ in $Q^1$ is $CHF_2$ or $CF_3$, specifically $CHF_2$.

In a preferred embodiment $R^1$ is selected from the group consisting of nitro, amino and $C_1$-$C_4$-alkylamino. More preferably, $R^1$ is nitro or amino. In particular, $R^1$ is nitro.

In a preferred embodiment, $R^2$ is chosen so that in organoboron compounds IV it does essentially not compete with Hal in compounds II. For instance, if $R^2$ is to be halogen, this halogen atom is preferably not more reactive than Hal in the compound II used, as otherwise the homocoupling of compounds IV would compete with the coupling of II and IV. If for examples Hal is Cl, $R^2$ is preferably not Br or I. Thus, in a preferred embodiment, if $R^2$ is to be halogen and Hal is Cl, $R^2$ is preferably F or Cl, in particular F; and if $R^2$ is to be halogen and Hal is Br, $R^2$ is preferably F, Cl or Br; in particular F or Cl.

In particular, $R^2$ is F or Cl.

Preferably, n is 1, 2 or 3; in particular 2 or 3.

More particularly, $R^2$ is F or Cl and n is 1, 2 or 3; in particular 2 or 3.

In a preferred embodiment, $R^3$ in compounds II is chosen so that it does essentially not compete with Hal. For instance, if Hal is Cl and $R^3$ is to be halogen, $R^3$ is preferably F; and if Hal is Br and $R^3$ is to be halogen, $R^3$ is preferably F or Cl.

In a particular embodiment, $R^3$ is hydrogen or fluorine.

In a particular embodiment, $R^1$ and $R^3$ (if the latter is different from hydrogen) are in para positions to one another.

In a particular embodiment, the biphenyl compound I is 4-chloro-2'-nitro-biphenyl, 3,4-dichloro-2'-nitro-biphenyl, 3,4-difluoro-2'-nitro-biphenyl, 3,4,5-trifluoro-2'-nitro-biphenyl, 3-chloro-4,5-difluoro-2'-nitro-biphenyl, 3,4-dichloro-5'-fluoro-2'-nitro-biphenyl, 3,5-dichloro-4-fluoro-2'-nitro-biphenyl, 4'-chloro-biphenyl-2-ylamine, 3',4'-dichloro-biphenyl-2-ylamine, 3',4'-difluoro-biphenyl-2-ylamine, 3',4',5'-trifluoro-biphenyl-2-ylamine, 3'-chloro-4',5'-difluoro-biphenyl-2-ylamine, 3',4'-dichloro-5-fluoro-biphenyl-2-ylamin or 3',5'-dichloro-4'-fluoro-biphenyl-2-ylamine.

Specifically, the biphenyl compound I is 4-chloro-2'-nitro-biphenyl, 3,4-dichloro-2'-nitro-biphenyl, 3,4-difluoro-2'-nitro-biphenyl, 3,4,5-trifluoro-2'-nitro-biphenyl, 3-chloro-4,5-difluoro-2'-nitro-biphenyl, 3,4-dichloro-5'-fluoro-2'-nitro-biphenyl or 3,5-dichloro-4-fluoro-2'-nitro-biphenyl. Very specifically, the biphenyl compound I is 3,4,5-trifluoro-2'-nitro-biphenyl.

The organoboron compound IV as defined under (i) in which o=0, m=2; p=1 and Z=OH is a boronic acid of formula IVa. Its trimer is a boroxine and has formula tri-IVa:

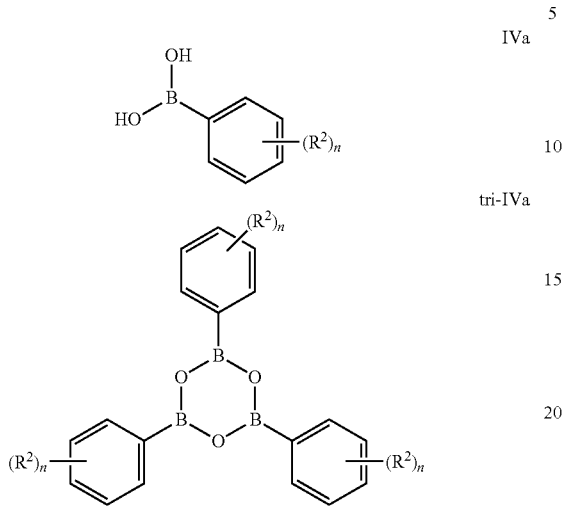

The boronic acid derivates as defined under (ii) with o=0, m=2; p=1 and Z=halogen; $C_1$-$C_4$-alkyl, $C_1$-$C_6$-alkoxy, $C_6$-$C_{10}$-aryl or $C_6$-$C_{10}$-aryloxy are compounds of formula IVb, wherein Z=halogen; $C_1$-$C_4$-alkyl, $C_1$-$C_6$-alkoxy, $C_6$-$C_{10}$-aryl or $C_6$-$C_{10}$-aryloxy:

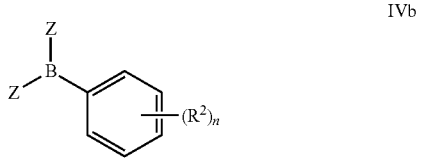

The borinic acids or borinic acid derivatives as defined under (iii) with o=0, m=1; p=2 and Z=hydroxy, halogen, $C_1$-$C_4$-alkyl, $C_1$-$C_6$-alkoxy, $C_6$-$C_{10}$-aryl or $C_6$-$C_{10}$-aryloxy are compounds of formula IVc (borinic acids) or compounds of formula IVd (borinic acid derivatives), wherein Z=halogen, $C_1$-$C_4$-alkyl, $C_1$-$C_6$-alkoxy, $C_6$-$C_{10}$-aryl or $C_6$-$C_{10}$-aryloxy:

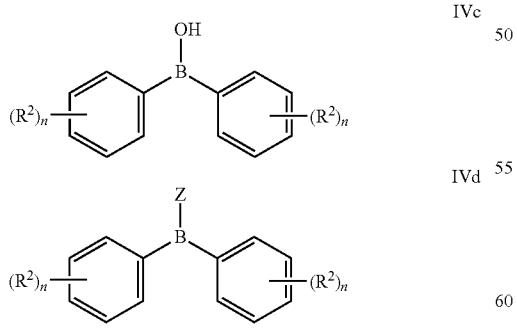

The mixed borinic acids or borinic acid derivatives as defined under (iv) with o=1, m=1; p=1, A=$C_1$-$C_4$-alkyl and Z=hydroxy, halogen, $C_1$-$C_4$-alkyl, $C_1$-$C_6$-alkoxy, $C_6$-$C_{10}$-aryl or $C_6$-$C_{10}$-aryloxy are compounds of formula IVe (mixed borinic acids) or compounds of formula IVf (mixed borinic acid derivatives), wherein Z=halogen, $C_1$-$C_4$-alkyl, $C_1$-$C_6$-alkoxy, $C_6$-$C_{10}$-aryl or $C_6$-$C_{10}$-aryloxy:

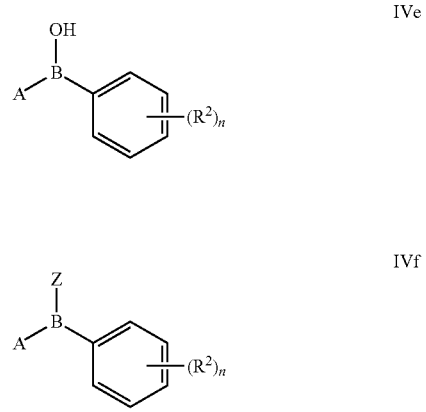

The cyclic boronic esters as defined under (v) with o=0, m=2 and p=1, wherein the two Z groups form together a bridging group —O—$(CH_2)_q$—O—, wherein q is 2 or 3, so that the two Z groups, together with the boron atom to which they are attached, form a 5- or 6-membered ring, where the $CH_2$ groups are optionally substituted by one or two $C_1$-$C_4$-alkyl groups are compounds of formula IVg:

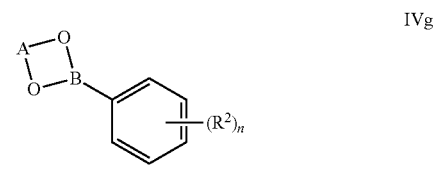

wherein A is —C($R^{A1}$)($R^{A2}$)—C($R^{A3}$)($R^{A4}$)— or —C($R^{A1}$)($R^{A2}$)—C($R^{A3}$)($R^{A4}$)—C($R^{A5}$)($R^{A6}$)—, where $R^{A1}$, $R^{A2}$, $R^{A3}$, $R^{A4}$, $R^{A5}$ and $R^{A6}$, independently of each other, are hydrogen $C_1$-$C_4$-alkyl.

The boronates as defined under (vi) with o=0, m=3, p=1 and Z=hydroxyl, halogen, $C_1$-$C_4$-alkyl, $C_1$-$C_6$-alkoxy, $C_6$-$C_{10}$-aryl or $C_6$-$C_{10}$-aryloxy, and accompanied by a cation which compensates the negative charge of the boronate anion are compounds of formula IVh, wherein each Z is independently hydroxyl, halogen, $C_1$-$C_4$-alkyl, $C_1$-$C_6$-alkoxy, $C_6$-$C_{10}$-aryl or $C_6$-$C_{10}$-aryloxy and $(M^{a+})_{1/a}$ is a cation equivalent:

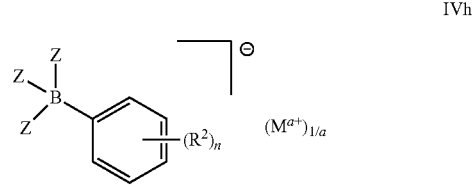

The triarylboranes as defined under (vii) with o=0, m=0 and p=3 are compounds of formula IVi:

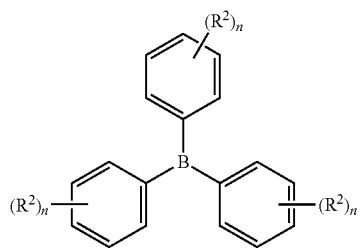

The tetraarylborates as defined under (viii) with o=0, m=0 and p=4, and accompanied by a cation which compensates the negative charge of the borate anion, are compounds of formula IVj, wherein $(M^{a+})_{1/a}$ is a cation equivalent:

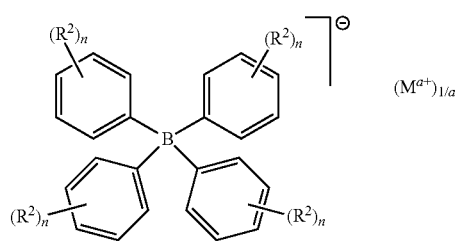

M in compounds IVh and IVj is preferably an alkali or earth alkaline metal cation or an ammonium cation $(NR^aR^bR^cR^d)+$, wherein $R^a$, $R^b$, $R^c$ and $R^d$, independently of each other, are hydrogen, $C_1$-$C_6$-alkyl or $C_1$-$C_6$-hydroxyalkyl. If M is an alkali metal cation or an ammonium cation, a is 1. If M is an earth alkaline metal cation, M is 2. More preferably, M is an alkali metal cation.

In the above organoboron compounds $R^2$ and n have one of the above general or, in particular, one of the above preferred meanings. In a particular embodiment, $(R_2)_n$ is 4-chloro, 3,4-dichloro, 3,4-difluoro, 3,4,5-trifluoro, 3-chloro-4,5-difluoro, 3,4-dichloro-5-fluoro or 3,5-dichloro-4-fluoro. The positions relate to the 1-position of the attachment of the phenyl ring to the boron atom.

A in the mixed borinic acids or borinic acid derivatives as defined under (iv) is in particular methyl.

Preferably, the organoboron compound IV is a phenylboronic acid IVa or a diphenylborinic acid IVc

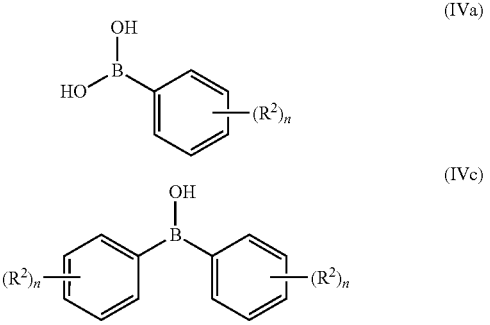

or a mixture of IVa and IVc, in which $R^2$ and n have one of the above general or, in particular, one of the above preferred meanings.

In a particular embodiment, $(R_2)_n$ in IVa and IVc is 4-chloro, 3,4-dichloro, 3,4-difluoro, 3,4,5-trifluoro, 3-chloro-4,5-difluoro, 3,4-dichloro-5-fluoro or 3,5-dichloro-4-fluoro. The positions relate to the 1-position of the attachment of the phenyl ring to the boron atom.

The organoboron compounds as defined under (i) to (viii) and methods for preparing them are known in the art and described, for example, in WO 2015/011032 and the literature cited therein.

The compounds of formulae II and IV are used in a molar ratio of preferably from 5:1 to 1:5, more preferably from 2:1 to 1:2, even more preferably from 1.5:1 to 1:1.5, in particular from 1.1:1 to 1:1.1, specifically from 1.05:1 to 1:1.05, and very specifically of approximately 1:1. "Approximately" is intended to include deviations from ideal stoichiometry caused for example, by weight errors. Such errors are in general below 10%, mostly below 5%. As however the removal of the halogen compound II from the reaction mixture after completion of the reaction is sometimes more difficult than the removal of the organoboron compound IV, it may be advantageous to use the organoboron compound IV in at least equivalent amounts, better in slight excess, so that the halogen compound II is reacted more or less completely. In this case, compounds of formulae II and IV are used in a molar ratio of preferably from 1:1 to 1:1.5, more preferably from 1:1 to 1:1.1, in particular from 1:1 to 1:1.05 and specifically from 1:1.01 to 1:1.05.

In the phosphorus ligand of formula Ill, $R^5$ is preferably $C_1$-$C_6$-alkyl. More preferably, $R^5$ is branched $C_3$-$C_6$-alkyl, such as isopropyl, sec-butyl, isobutyl, tert-butyl, 1-ethyl-1-methyl-prop-1-yl, 1,1-dimethyl-prop-1-yl and the like. Specifically, $R^5$ is tert-butyl.

Preferably, $R^6$, $R^7$ and $R^8$, independently of each other, are selected from the group consisting of hydrogen, methyl, trifluoromethyl or methoxy.

Alternatively preferably, $R^6$ and $R^7$, or $R^7$ and $R^8$, together with the carbon atoms they are bound to, form a 5- or 6-membered partially unsaturated or maximally unsaturated carbocyclic or heterocyclic ring, where the heterocyclic ring contains 1, 2, 3 or 4 heteroatoms or heteroatom groups selected from N, O, NO and $SO_2$ as ring members; where the carbocyclic or heterocyclic ring may carry one or more substituents selected from methyl, trifluoromethyl and methoxy. More preferably, $R^6$ and $R^7$, or $R^7$ and $R^8$, together with the carbon atoms they are bound to, form a phenyl ring (i.e. $R^6$ and $R^7$ or $R^7$ and $R^8$ are together —CH=CH—CH=CH—), where the thusly formed ring may carry one or more substituents selected from methyl, trifluoromethyl and methoxy. The radical $R^6$, $R^7$ and $R^8$ not forming part of the ring is preferably selected from hydrogen, methyl, trifluoromethyl and methoxy.

In particular however, $R^6$, $R^7$ and $R^8$ are hydrogen.

Preferably, $R^9$, $R^{10}$ are each independently selected from the group consisting of hydrogen and $C_1$-$C_6$-alkyl, more preferably from hydrogen and methyl, and are specifically both hydrogen.

Preferably, $R^{11}$, $R^{12}$, $R^{13}$, $R^{14}$ and $R^{15}$, independently of each other, are selected from the group consisting of hydrogen, halogen, $C_1$-$C_6$-alkyl, trifluoromethyl and $C_1$-$C_6$-alkoxy;

or any two adjacent instances of $R^{11}$, $R^{12}$, $R^{13}$, $R^{14}$, $R^{15}$ (i.e. $R^{11}$ and $R^{12}$, or $R^{12}$ and $R^{13}$, or $R^{13}$ and $R^{14}$, or $R^{14}$ and $R^{15}$, together with the carbon atoms to which they are bound, form a five- or six-membered partially unsaturated or maximally unsaturated carbocyclic or heterocyclic ring, where the heterocyclic ring contains 1, 2, 3 or 4 heteroatoms or heteroatom groups selected from N, O, NO and SO$_2$ as ring members; where the carbocyclic or heterocyclic ring may carry one or more substituents selected from trifluoromethyl, C$_1$-C$_6$-alkyl, C$_1$-C$_6$-alkoxy, C$_3$-C$_{10}$-cycloalkyl, C$_6$-C$_{10}$-aryl, 5- to 11-membered saturated, partially unsaturated or maximally unsaturated heterocyclyl containing 1, 2, 3 or 4 heteroatoms or heteroatom groups selected from N, O, NO and SO$_2$ as ring members, and NR$^{16}$R$^{17}$, wherein the above C$_3$-C$_{10}$-cycloalkyl, 5- to 11-membered heterocyclyl and C$_6$-C$_{10}$-aryl groups are optionally substituted with 1, 2 or 3 substituents independently selected from the group consisting of C$_1$-C$_6$-alkyl, C$_1$-C$_6$-alkoxy and trifluoromethyl.

More preferably, two adjacent instances of R$^{11}$, R$^{12}$, R$^{13}$, R$^{14}$, R$^{15}$, together with the carbon atoms to which they are bound, form a five- or six-membered partially unsaturated or maximally unsaturated carbocyclic or heterocyclic ring, where the heterocyclic ring contains 1, 2, 3 or 4 heteroatoms or heteroatom groups selected from N, O, NO and SO$_2$ as ring members; where the carbocyclic or heterocyclic ring may carry one or more substituents selected from trifluoromethyl, C$_1$-C$_6$-alkyl, C$_1$-C$_6$-alkoxy, C$_3$-C$_{10}$-cycloalkyl, C$_6$-C$_{10}$-aryl, 5- to 11-membered saturated, partially unsaturated or maximally unsaturated heterocyclyl containing 1, 2, 3 or 4 heteroatoms or heteroatom groups selected from N, O, NO and SO$_2$ as ring members, and NR$^{16}$R$^{17}$, wherein the above C$_3$-C$_{10}$-cycloalkyl, 5- to 11-membered heterocyclyl and C$_6$-C$_{10}$-aryl groups are optionally substituted with 1, 2 or 3 substituents independently selected from the group consisting of C$_1$-C$_6$-alkyl, C$_1$-C$_6$-alkoxy and trifluoromethyl. That or those radical(s) which do not form a ring are preferably selected from hydrogen and methyl, and are in particular hydrogen.

Even more preferably, both R$^{11}$ and R$^{12}$, as well as R$^{14}$ and R$^{15}$, together with the carbon atoms to which they are bound, form a five- or six-membered partially unsaturated or maximally unsaturated carbocyclic or heterocyclic ring, where the heterocyclic ring contains 1, 2, 3 or 4 heteroatoms or heteroatom groups selected from N, O, NO and SO$_2$ as ring members; where the carbocyclic or heterocyclic ring may carry one or more substituents selected from trifluoromethyl, C$_1$-C$_6$-alkyl, C$_1$-C$_6$-alkoxy, C$_3$-C$_{10}$-cycloalkyl, C$_6$-C$_{10}$-aryl, 5- to 11-membered saturated, partially unsaturated or maximally unsaturated heterocyclyl containing 1, 2, 3 or 4 heteroatoms or heteroatom groups selected from N, O, NO and SO$_2$ as ring members, and NR$^{16}$R$^{17}$, wherein the above C$_3$-C$_{10}$-cycloalkyl, 5- to 11-membered heterocyclyl and C$_6$-C$_{10}$-aryl groups are optionally substituted with 1, 2 or 3 substituents independently selected from the group consisting of C$_1$-C$_6$-alkyl, C$_1$-C$_6$-alkoxy and trifluoromethyl. In this case, R$^{13}$ is preferably selected from hydrogen and methyl, and is in particular hydrogen.

In particular, both R$^{11}$ and R$^{12}$, as well as R$^{14}$ and R$^{15}$, together with the carbon atoms to which they are bound, form a phenyl ring (i.e. R$^{11}$ and R$^{12}$ form together a bridging group —CH═CH—CH═CH—, and R$^{14}$ and R$^{15}$ form together a bridging group —CH═CH—CH═CH—, so that the phenyl ring carrying R$^{11}$, R$^{12}$, R$^{14}$ and R$^{15}$ is in sum an anthracenyl ring). In this case, R$^{13}$ is preferably selected from hydrogen and methyl, and is in particular hydrogen.

Specifically, the phosphorus ligand III is a compound of formula IIIa

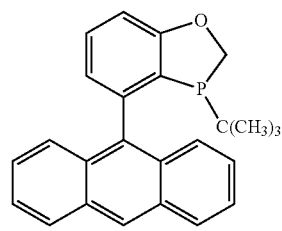

(IIIa)

Ligands III and methods for preparing them are principally known and described, for example, in WO 2011/126917, G. Xu et al., J. Am. Chem. Soc. 2014, 136, 570-573, Q. Zhao, Chem. Eur. J. 2013, 19, 2261-2265 and the literature cited therein.

The palladium source for the palladium complex is preferably a palladium(II) salt, a palladium(II) complex or a palladium(0) source.

The palladium catalyst can be introduced into the reaction for example in form of a pre-formed complex of palladium (0) and the ligand Ill, in form of a palladium(II) salt and the ligand Ill, in form of a palladium(II) complex and the ligand Ill, or in form of a palladium(0) source and the ligand Ill. In the latter three cases, the complex with the ligand (III) is either formed before the Suzuki reaction starts or, in particular, is formed in situ. In case of the Pd(II) salt or complex, Pd(II) is reduced to Pd(0) before the Suzuki reaction starts or in situ.

Suitable Pd(II) salts are for example Pd(II) acetate, PdCl$_2$ or Na$_2$PdCl$_4$. Preference is given to Pd(II) acetate and PdCl$_2$. In particular, Pd(II) acetate is used. Suitable Pd(II) complexes are for example Pd(II) acetylacetonate or bisacetonitrile Pd(II) chloride. A suitable Pd(0) source is metallic palladium, optionally on a carrier, such as charcoal.

Preferably, the palladium catalyst is introduced into the reaction in form of a palladium(II) salt and the ligand III.

If the palladium catalyst is not introduced into the reaction in form of the pre-formed complex of palladium(0) and the ligand III, but in form of a Pd source (e.g. a palladium(II) salt, a palladium(II) complex with ligands different from III or a palladium(0) source), the Pd source (calculated on the basis of the Pd content) and the ligand of formula III are used in a molar ratio of preferably from 5:1 to 1:5, more preferably from 2:1 to 1:2, even more preferably from 1.5:1 to 1:1.5, in particular from 1.1:1 to 1:1.1, specifically from 1.05:1 to 1:1.05, very specifically approximately 1:1. "Approximately" is intended to include deviations from ideal stoichiometry caused for example, by weight errors. Such errors are in general below 10%, mostly below 5%.

The Pd source (calculated on the basis of the Pd content) can principally be used in an amount of up to 5 mol %, e.g. of from 0.0001 mol % to 5 mol %, relative to 1 mol of compound II or of compound IV (1 mol of compound II or of compound IV corresponding to 100%). If compounds II and IV are not used in equimolar amounts, the above mol % relate to 1 mol of that compound II or IV which is not used in excess. The ligand III and the other reaction conditions allow however for the use of Pd in significantly lower amounts. Thus, preferably, the Pd source (calculated on the basis of the Pd content) is used in an amount of from 0.0001 mol % to 0.5 mol %, more preferably from 0.0001 mol % to 0.1 mol %, in particular from 0.0001 mol % to 0.01 mol %, and specifically from 0.001 mol % to 0.01 mol %, e.g. from 0.003 to 0.007 mol %, relative to 1 mol of compound II or of compound IV (1 mol of compound II or of compound IV corresponding to 100%). If compounds II and IV are not used in equimolar amounts, the above mol % relate to 1 mol of that compound II or IV which is not used in excess.

The method of the invention is characterized by being carried out in a solvent mixture of water, a non-polar organic solvent and a polar aprotic co-solvent.

Non-polar organic solvents are for example aliphatic hydrocarbons, such as alkanes, e.g. pentane, hexane, heptane, octane, mixtures thereof and technical mixtures, such as petrol ether; cycloaliphatic hydrocarbons, such as cycloalkanes, e.g. cyclohexane, cycloheptane, or cyclooctane; chlorinated aliphatic hydrocarbons, such as halogenalkanes, e.g. dichloromethane, trichloromethane, tetrachloromethane, dichloroethane or tetrachloroethane, aromatic hydrocarbons, such as benzene, toluene, the xylenes, ethylbenzene, cumene (isopropylbenzene), chlorobenzene, o-dichlorobenzene or nitrobenzene, or open-chained ethers, such as diethylether, dipropylether, methyl-tert-butylether or methyl-isobutylether.

Preferably, the non-polar organic solvent is an aromatic hydrocarbon, such as benzene, toluene, the xylenes, ethylbenzene, cumene (isopropylbenzene), chlorobenzene, o-dichlorobenzene or nitrobenzene. Among these, preference is given to toluene and the xylenes. In particular, toluene is used.

In terms of the present invention, polar aprotic solvents are solvents which at 20° C. are water-miscible in the desired ratios of water/polar aprotic solvent to be used. Moreover, polar aprotic solvents are solvents without a functional group from which a proton can dissociate. "Miscible" means that a homogenous solution is formed. Examples for suitable polar aprotic solvents are amides, such as N,N-dimethylformamide (DMF) and N,N-dimethylacetamide; sulfoxides, such as dimethylsulfoxide (DMSO); lactams, such as N-methylpyrrolidone (NMP); cyclic ethers, such as tetrahydrofuran, 1,3-dioxane and 1,4-dioxane; ketones, such as acetone and methylethylketone; nitriles, such as acetonitrile; lactones, such as γ-butyrolactone; nitro compounds, such as nitromethane; ureas, such as tetramethyl urea or dimethylpropylene urea (DMPU); sulfones, such as sulfolan; and carbonic acid esters, such as dimethylcarbonate or ethylenecarbonate.

Preferably, the polar aprotic co-solvent is a cyclic ether, such as tetrahydrofuran, 1,3-dioxane and 1,4-dioxane, and is in particular tetrahydrofuran.

Preferably, in the solvent mixture water, the non-polar organic solvent and the polar aprotic co-solvent are contained in following amounts:
water: 0.5 to 20% by weight, based on the total weight of the solvent mixture;
non-polar organic solvent: 20 to 99% by weight, based on the total weight of the solvent mixture; and
polar aprotic co-solvent: 1 to 60% by weight, based on the total weight of the solvent mixture;
where the amounts of water, non-polar organic solvent and polar aprotic co-solvent add to 100% by weight.

More preferably, water, the non-polar organic solvent and the polar aprotic co-solvent are contained in following amounts:
water: 1 to 15% by weight, based on the total weight of the solvent mixture;
non-polar organic solvent: 60 to 96% by weight, based on the total weight of the solvent mixture; and
polar aprotic co-solvent: 3 to 25% by weight, based on the total weight of the solvent mixture;
where the amounts of water, non-polar organic solvent and polar aprotic co-solvent add to 100% by weight.

Even more preferably, water, the non-polar organic solvent and the polar aprotic co-solvent are contained in following amounts:
water: 1 to 11% by weight, based on the total weight of the solvent mixture;
non-polar organic solvent: 75 to 94% by weight, based on the total weight of the solvent mixture; and
polar aprotic co-solvent: 4 to 17% by weight, based on the total weight of the solvent mixture;
where the amounts of water, non-polar organic solvent and polar aprotic co-solvent add to 100% by weight.

In particular, water, the non-polar organic solvent and the polar aprotic co-solvent are contained in following amounts:
water: 1 to 10% by weight, based on the total weight of the solvent mixture;
non-polar organic solvent: 75 to 90% by weight, based on the total weight of the solvent mixture; and
polar aprotic co-solvent: 8 to 16% by weight, based on the total weight of the solvent mixture;
where the amounts of water, non-polar organic solvent and polar aprotic co-solvent add to 100% by weight.

In particular the solvent mixture in which the Suzuki reaction is carried out does not contain any other solvent than water, the non-polar organic solvent and the polar aprotic co-solvent.

The Suzuki reaction is carried out in the presence of a base. Suitable are both inorganic and organic bases.

Suitable inorganic bases are for example from alkali metal carbonates, e.g. $Li_2CO_3$, $Na_2CO_3$, $K_2CO_3$ or $Cs_2CO_3$, earth alkaline metal carbonates, e.g. $MgCO_3$ or $CaCO_3$, alkali metal phosphates, e.g. $Li_3PO_4$, $Na_3PO_4$, $K_3PO_4$ or $Cs_3PO_4$, earth alkaline metal phosphates, e.g. $Mg_3(PO_4)_2$ or $Ca_3(PO_4)_2$, alkali metal hydrogenphosphates, e.g. $Li_2HPO_4$, $Na_2HPO_4$, $K_2HPO_4$ or $Cs_2HPO_4$, earth alkaline metal hydrogenphosphates, e.g. $MgHPO_4$ or $CaHPO_4$, alkali metal hydroxides, LiOH, NaOH or KOH, and earth alkaline metal hydroxides, e.g. $Mg(OH)_2$ or $Ca(OH)_2$.

Examples for suitable organic bases are open-chained amines, e.g. trimethylamine, triethylamine, tripropylamine, ethyldiisopropylamine and the like, or basic N-heterocycles, such as morpholine, pyridine, lutidine, DABCO, DBU or DBN.

Preference is however given to inorganic bases, such as to the above alkali metal carbonates, earth alkaline metal carbonates, alkali metal phosphates, earth alkaline metal phosphates, alkali metal hydrogenphosphates, earth alkaline metal hydrogenphosphates, alkali metal hydroxides and earth alkaline metal hydroxides. More preferred are alkali metal carbonates, such as the above-mentioned $Li_2CO_3$, $Na_2CO_3$, $K_2CO_3$ or $Cs_2CO_3$. In particular, $Na_2CO_3$ or $K_2CO_3$ are used. Specifically, $K_2CO_3$ is used.

The base is preferably used in an amount 0.1 to 5 mol per mol of compound II or IV, more preferably from 0.5 to 3 mol per mol of compound II or IV, in particular from 1 to 2 mol per mol of compound II or IV. If compounds II and IV are not used in equimolar amounts, the above relation is to 1 mol of that compound II or IV which is not used in excess.

The reaction temperature is not very critical and can for example be in the range of from 0 to 200° C. Elevated temperature is however advantageous for a reasonable reaction rate. Thus, the reaction is preferably carried out at an elevated temperature, such as from 40 to 200° C., more preferably from 50 to 140° C., in particular from 90 to 130° C.

The reaction pressure is principally not critical. As however elevated temperatures are preferred and in case that the solvents used have a boiling point beneath the desired temperature, the reaction is in this case generally carried out in a closed vessel. This results in an inherent pressure, which is generally in the range of from 1.1 to 10 bar, in particular from 1.5 to 5 bar, specifically from 2 to 3 bar. The exertion of additional pressure, e.g. by pressurizing with an inert gas, is not necessary.

The reaction can be carried out by standard proceedings for Suzuki reactions, e.g. by mixing all reagents, inclusive catalyst or catalyst precursor and ligand, base and the solvent mixture, and reacting them at the desired temperature. Alternatively the reagents can be added gradually, especially in the case of a continuous or semicontinuous process. The reaction is preferably carried out in an inert atmosphere in order to avoid the presence of oxygen, e.g. under an argon or nitrogen atmosphere.

If the reaction is to be carried out at elevated temperature, e.g. above 40° C., the reaction is preferably carried out in a pressure vessel, e.g. an autoclave.

After completion of the reaction, the reaction mixture is worked up and the compound of the formula I is isolated in a customary manner. For example, the solvents are removed, for example under reduced pressure. Preferably, however, the work-up is effected by adding water to the reaction mixture and separating the two phases (aqueous and organic phase). The product I is in the organic phase mainly formed by the non-polar organic solvent. Moreover, the organic phase also contains the Pd catalyst. To enhance the yield, the aqueous phase can be extracted once or more times with an organic solvent, such as the above listed non-polar organic solvents. The product I is then separated from the catalyst and optionally from other undesired components, such as unreacted starting compounds II and/or IV, via customary means. For example, the compound I is crystallized from the organic phase. Alternatively, the solvent is removed from the organic phase, e.g. by distillation, e.g. under vacuum, optionally after drying the organic phase, and the solid matter is taken up in another solvent in which the compound I crystallizes better. In yet another alternative, the solid matter is submitted to a chromatographic separation.

Further purification of the product I can be effected if desired; for example by extraction, crystallization, distillation or by chromatography.

If desired, and if $R^1$ in the obtained compound I is not —NH—CO—R' with R'=$Q^1$, $Q^2$ or $Q^3$, the compound I can then be converted into final products. For instance, compounds I, wherein $R^1$ is nitro, amino, —N(H)PG, —NH—CO—R' or —N=CR'R", can be converted into carboxamides of the formula V

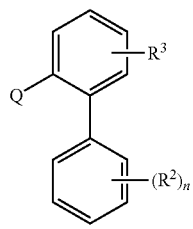

(V)

where Q is $Q^1$, $Q^2$ or $Q^3$, where $Q^1$, $Q^2$ and $Q^3$ are as defined above, and where $R^2$, $R^3$ and n have one of the above general, or, in particular, one of the above preferred meanings.

In case that $R^1$ is nitro, this is expediently first reduced to the respective amino group $NH_2$.

Reduction may be carried out with hydrogen in the presence of a hydrogenation catalyst or with other reduction agents, such as $SnCl_2$/HCl, Fe/HCl or Fe/N $H_4$Cl.

Reduction can be carried out according to known methods of converting aromatic nitro compounds into the corresponding aromatic amino compounds, such as described, for example, in R. J. Rahaim, R. E. Maleczka (Jr.), Org. Lett., 2005, 7, 5087-5090, G. S. Vanier, Synlett, 2007, 131-135, S. Chandrasekhar, S. Y. Prakash, C. L. Rao, J. Org. Chem., 2006, 71, 2196-2199, H. Berthold, T. Schotten, H. Hönig, Synthesis, 2002, 1607-1610, and C. Yu, B. Liu, L. Hu, J. Org. Chem., 2001, 66, 919-924.

In case that $R^1$ is-N(H)PG, —NH—CO—R' or —N=CR'R", these groups are expediently first reacted (deprotected) to amino compounds I with $R^1$=$NH_2$.

Deprotection conditions depend on the specific protective groups PG, C(O)R' or =CR'R" and are known in the art; examples of which may be found in T. Greene and P. Wuts, Protective Groups in Organic Synthesis ($3^{rd}$ ed.), John Wiley & Sons, NY (1999). For instance, benzyl groups are cleaved under hydrogenolysis, suitably in the presence of a hydrogenation catalyst, such as Pd. Alternatively, and avoiding hydrogenolysis, the benzyl protective group can be first converted into a carbamate group which can be removed by acid, neutral or basic treatment, such as ethoxycarbonyl or 1-chloroethoxycarbonyl. Conversion of the benzyl group is for example carried out by reaction with the respective carbonic ester chloride. Boc is generally removed under acidic conditions, etc.

To obtain compounds V, the amino compound I ($R^1$=$NH_2$) is subjected to an N-acylation with an acyl precursor of radicals $Q^1$, $Q^2$ or $Q^3$ to obtain a compound of formula V.

Suitable acyl precursors are compounds $Q^{11}$, $Q^{22}$ or $Q^{33}$

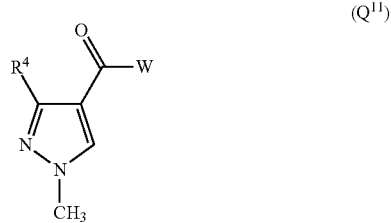

($Q^{11}$)

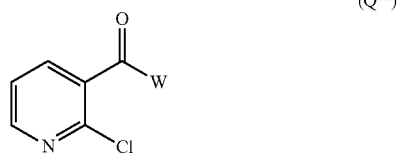

($Q^{22}$)

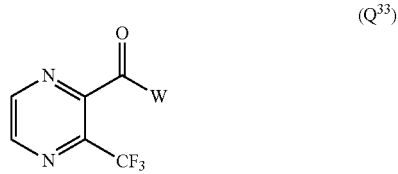

($Q^{33}$)

wherein $R^4$ has one of the above general, or, in particular, one of the above preferred meanings and W is —OH, a halide, especially chloride or bromide, —$OR^A$, or —O—C(O)—$R^B$.

If compounds $Q^{11}$, $Q^{22}$ or $Q^{33}$ are acids, i.e. W=OH, the reaction can be performed in the presence of a coupling reagent. Suitable coupling reagents (activators) are well known in the art.

If W=halide, the reaction is expediently performed in the presence of a base. Suitable bases are those listed above in context with the Suzuki coupling.

If W=OR$^A$, the compounds $Q^{11}$, $Q^{22}$ or $Q^{33}$ are esters. Suitable esters derive preferably from $C_1$-$C_4$-alkanols R$^A$OH in which R$^A$ is $C_1$-$C_4$-alkyl, or from $C_2$-$C_6$-polyols such as glycol, glycerol, trimethylolpropane, erythritol, pentaerythritol and sorbitol. Alternatively, the ester is a so-called active ester, which is obtained in a formal sense by the reaction of the acid $Q^{11}$, $Q^{22}$ or $Q^{33}$ (W=OH) with an active ester-forming alcohol, such as p-nitrophenol, N-hydroxybenzotriazole (HOBt), N-hydroxysuccinimide or OPfp (pentafluorophenol).

If compounds $Q^{11}$, $Q^{22}$ or $Q^{33}$ are anhydrides, i.e. W=O—C(O)—R$^B$, these are either a symmetric anhydride or an asymmetric anhydride in which —O—OC—R$^B$ is a group which can be displaced easily by the 2-aminobiphenyl (I) used in the reaction. Suitable acid derivatives with which the carboxylic acid $Q^{11}$, $Q^{22}$ or $Q^{33}$ with W=OH can form suitable mixed anhydrides are, for example, the esters of chloroformic acid, for example isopropyl chloroformate and isobutyl chloroformate, or of chloroacetic acid.

The acylation can be carried out under known conditions.

The method of the invention yields compounds I in high yields and requires distinctly lower amounts of Pd than most prior art processes. Moreover, the Suzuki reaction proceeds very selectively, effectively suppressing homocoupling reactions. The process is very well suited for large scale production, and the workup is very simple. Moreover, as the required amounts of Pd are so low, the catalyst does not need to be recycled, which is a very time-consuming and costly procedure, but can be disposed after the reaction.

The invention is further illustrated by the following examples.

EXAMPLES

Example 1: Synthesis of 3,4,5-trifluoro-2'-nitrobiphenyl

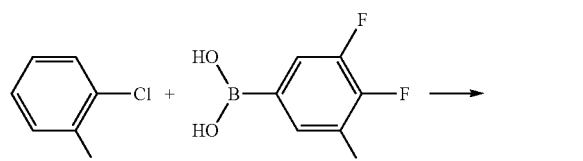

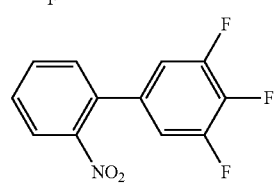

88.8 g (99 wt %, 0.50 mol, 1.0 eq) of solid (3,4,5-trifluorophenyl)boronic acid were placed in a reactor together with 441 g of toluene, 44.8 of water, 77 g of THF and 138.0 g (1.00 mol, 2.0 eq) of potassium carbonate. Finally 151.0 g of ortho-chloro-nitrobenzene (o-CNB; 50% in toluene, 0.48 mol, 0.96 eq) were added and 3 bar of nitrogen pressure was applied as a pressure test of the vessel. After releasing the pressure, 6.0 mg (0.027 mmol, 0.0054 mol %, relative to the boronic acid) of palladium acetate and 10.0 mg (0.027 mmol, 0.0054 mol %, relative to the boronic acid) AntPhos (phosphorus ligand of formula IIIa) were added. The reactor was evacuated twice to 200 mbar and each time refilled with nitrogen. Finally, the reactor was evacuated again to 200 mbar and the temperature was raised to 110° C. jacket temperature in 30 minutes. The temperature was kept at 110° C. for 6 h. The reactor was cooled to 25° C., the pressure released, 540 g of water were added and the phases were separated. The organic phase (736 g) was assayed for the desired biphenyl by quantitative HPLC. The organic phase contained 16.4 wt % of the title compound (120.7 g, 0.477 mol, 95.4%; yield percentage based on o-CNB).

HPLC Method:

Zorbax XDB-C18 1.8 µm; 50×4.6 mm; mobile phase: A: water+0.1% phosphoric acid; B: acetonitrile (MeCN)+0.1% phosphoric acid; gradient: 30% to 50% B in 5.0 minutes; 50% to 100% B in 1.0 min; 100% B 2.0 min; flow: 1.5 mL/min, pressure 240 bar, temperature 30° C.

Retention time of 3,4,5-trifluoro-2'-nitrobiphenyl: 6.4 min

The examples in table 1 were carried out analogously, however with the amounts of ortho-chloronitrobenzene (o-CNB; amount given in mol equivalents, relative to 1 mol of the boronic acid), potassium carbonate (amount given in mol equivalents, relative to 1 mol of the boronic acid) and solvents and the reaction temperature as shown in each line of table 1, respectively.

TABLE 1

| Example | o-CNB eq. | $K_2CO_3$ eq. | Toluene [g] | Water [g] | THF [g] | T [° C.] | Yield [%]* |
|---|---|---|---|---|---|---|---|
| Comp-1 | 0.96 | 2 | 981 | 19 | — | 130 | 36.5 |
| Comp-2 | 0.96 | 2 | 900 | — | 99 | 130 | 37.5 |
| Comp-3 | 0.96 | 2 | 981 | — | — | 130 | 16.7 |
| 1 | 0.96 | 2 | 931.9 | 18.6 | 96 | 130 | 92.3 |
| 2 | 0.96 | 2 | 594 | 42 | 74 | 130 | 95.8 |
| 3 | 0.96 | 2 | 441 | 44.8 | 77 | 110 | 99.4 |
| 4 | 0.96 | 2 | 404.5 | 48.5 | 80.9 | 110 | 99.7 |
| 5 | 0.98 | 2 | 503 | 45.3 | 75.5 | 110 | 100.3** |
| 6 | 0.98 | 1 | 503 | 45.3 | 75.5 | 110 | 101.9** |
| 7 | 1 | 1.2 | 604 | 54.3 | 90.6 | 130 | 98.7# |

*based on o-CNB
**yield over 100% due to analytic fluctuation
4 h reaction time As the comparative examples Comp-1, Comp-2 and Comp-3 show, omitting water or THF or both results in a significantly lowered yield.

Example 2: Efficiency of the Ligand of Formula III

In order to show the importance of the ligand used according to the invention, (3,4,5-trifluorophenyl)boronic acid and ortho-chloro-nitrobenzene were reacted in a mixture of toluene, water and THF in the presence of potassium carbonate and a Pd catalyst under analogous conditions, using however different ligands for the Pd catalyst.

TABLE 2

| Example | Ligand | Conversion [%] | Yield [%] |
|---|---|---|---|
| 11 | AntPhos (compound IIIa) | 100 | 97.2 |
| Comp-4 | triphenylphosphine | 22.5 | 0.3 |
| Comp-5 | dppe | 23.9 | 0.5 |
| Comp-6 | dppf | 23.1 | 0.7 |
| Comp-7 | Pepstar | 23.6 | 1.3 |
| Comp-8 | tricyclohexylphosphine | 26.7 | 2.4 |
| Comp-9 | Xantphos | 26.9 | 0.7 |

TABLE 2-continued

| Example | Ligand | Conversion [%] | Yield [%] |
|---------|--------|----------------|-----------|
| Comp-13 | cBRIDP | 26.7 | 0.5 |
| Comp-19 | RockPhos | 27.1 | 0.5 |
| Comp-21 | PhenCar-Phos | 35.8 | 8.8 |
| Comp-23 | Unnicore CX21# | 55.5 | 14.3 |
| Comp-24 | Unnicore CX31# | 53.7 | 6.3 |

Pd complex used
dppe: 1,2-Bis(diphenylphosphino)ethane
dppf: 1,1'-Bis(diphenylphosphino)ferrocene
Pepstar: 2,2-Dimethyl-1,3-bis(diphenylphosphinopropane)
Xantphos: 4,5-Bis(diphenylphosphino)-9,9-dimethylxanthene
cBRIDP: Di-tert-butyl(2,2-diphenyl-1-methyl-1-cyclopropyl)phosphine, Mo-Phos
RockPhos: [(2-Di-tert-butylphosphino-3-methoxy-6-methyl-2',4',6'-triisopropyl-1,1'-biphenyl)-2-(2-aminobiphenyl)]palladium (II) methanesulfonate
PhenCar-Phos: 9-[2-(Di-i-propylphosphino)phenyl]-9H-carbazole
Umicore CX21: Allylchloro[1,3-bis(2,6-diisopropylphenyl)imidazol-2-ylidene]palladium (II)
Umicore CX31: Chlorophenylallyl[1,3-bis(2,6-diisopropylphenyl)imidazol-2-ylidene]palladium (II)

The invention claimed is:

1. A process for preparing substituted biphenyls of the formula I

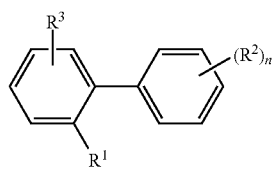
(I)

in which the substituents are each defined as follows:
$R^1$ is nitro, amino, $C_1$-$C_4$-alkylamino, —N(H)PG, —NH—CO—R', —N=CR'R" or a moiety of the formula $Q^1$, $Q^2$ or $Q^3$

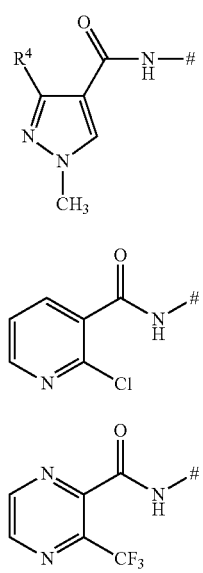

with
PG being a protective group;
R' and R" being independently of each other and independently of each occurrence $C_1$-$C_4$-alkyl or phenyl which may carry 1, 2 or 3 substituents selected from the group consisting of halogen, $C_1$-$C_4$-alkyl, $C_1$-$C_4$-haloalkyl, $C_1$-$C_4$-alkoxy and $C_1$-$C_4$-haloalkoxy;
$R^4$ being methyl, optionally substituted by 1, 2 or 3 fluorine atoms; and
being the attachment point to the remainder of the molecule;
$R^2$ is selected from the group consisting of cyano, nitro, halogen, $C_1$-$C_4$-alkyl, $C_1$-$C_4$-haloalkyl, $C_1$-$C_4$-alkoxy, $C_1$-$C_4$-haloalkoxy, $C_3$-$C_{10}$-cycloalkyl which may carry 1, 2, 3 or 4 $C_1$-$C_4$-alkyl substituents; $C_3$-$C_{10}$-halocycloalkyl, $C_1$-$C_6$-alkoxy, $C_1$-$C_6$-haloalkoxy, $C_1$-$C_6$-alkylcarbonyl; $C_1$-$C_6$-haloalkylcarbonyl; $C_1$-$C_6$-alkoxycarbonyl; $C_1$-$C_6$-haloalkoxycarbonyl; aryl; aryl-$C_1$-$C_4$-alkyl; arylcarbonyl; aryl-$C_1$-$C_4$-alkylcarbonyl; aryloxycarbonyl; aryl-$C_1$-$C_4$-alkoxycarbonyl, wherein aryl in the six last-mentioned radicals may carry 1, 2, 3 or 4 substituents selected from halogen, cyano, nitro, $C_1$-$C_4$-alkyl, $C_1$-$C_4$-haloalkyl, $C_1$-$C_4$-alkoxy and $C_1$-$C_4$-haloalkoxy; aminocarbonyl, $C_1$-$C_4$-alkylaminocarbonyl, and di-($C_1$-$C_4$-alkyl)-aminocarbonyl;
n is 0, 1, 2 or 3, where, in case that n=2 or 3, the $R^2$ radicals may have identical or different definitions; and
$R^3$ is hydrogen, cyano, halogen, $C_1$-$C_4$-alkyl, $C_1$-$C_4$-haloalkyl or $C_1$-$C_4$-alkoxy;
which comprises reacting a compound of the formula II

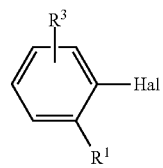
(II)

in which Hal is chlorine or bromine and $R^1$ and $R^3$ are each as defined above,
in the presence of a base and of a palladium catalyst which comprises a palladium source and a phosphorus ligand of the formula III

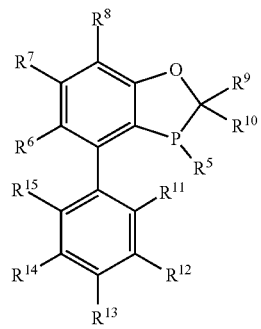
(III)

in which
$R^5$ is $C_1$-$C_6$-alkyl, trifluoromethyl, $C_6$-$C_{10}$-aryl or 5- to 10-membered heteroaryl containing 1, 2, 3 or 4 heteroatoms selected from the group consisting of N and O as ring members;
$R^6$, $R^7$, $R^8$ are each independently selected from the group consisting of hydrogen, trifluoromethyl, $C_1$-$C_6$-alkyl, $C_1$-$C_6$-alkoxy, $C_3$-$C_{10}$-cycloalkyl, 5- to 11-membered saturated, partially unsaturated or maximally unsaturated heterocyclyl containing 1, 2, 3 or 4 heteroatoms or heteroatom groups selected from the group consisting of N, O, NO and $SO_2$ as ring members, $C_6$-$C_{10}$-aryl and $NR^{16}R^{17}$, wherein the above $C_3$-$C_{10}$-cycloalkyl, 5- to 11-membered heterocyclyl and $C_6$-$C_{10}$-aryl groups are optionally substituted with 1, 2 or 3 substituents independently selected from the group consisting of $C_1$-$C_6$-alkyl, $C_1$-$C_6$-alkoxy and trifluoromethyl; or $R^6$ and $R^7$, or $R^7$ and $R^8$, together with the carbon atoms they are bound to, form a 5- or 6-membered partially unsaturated or maximally unsaturated carbocyclic or heterocyclic ring, where the heterocyclic ring contains 1, 2, 3 or 4 heteroatoms or heteroatom groups selected from N, O, NO and $SO_2$ as ring members; where the carbocyclic or heterocyclic ring may carry one or more substituents selected from the group consisting of trifluoromethyl, $C_1$-$C_6$-alkyl, $C_1$-$C_6$-alkoxy, $C_3$-$C_{10}$-cycloalkyl, 5- to 11-membered saturated, partially unsaturated or maximally unsaturated heterocyclyl containing 1, 2, 3 or 4 heteroatoms or heteroatom groups selected from N, O, NO and $SO_2$ as ring members, $C_6$-$C_{10}$-aryl and $NR^{16}R^{17}$, wherein the above $C_3$-$C_{10}$-cycloalkyl, 5- to 11-membered heterocyclyl and $C_6$-$C_{10}$-aryl groups are optionally substituted with 1, 2 or 3 substituents independently selected from the group consisting of $C_1$-$C_6$-alkyl, $C_1$-$C_6$-alkoxy and trifluoromethyl;

$R^9$, $R^{10}$ are each independently selected from the group consisting of hydrogen, $C_1$-$C_6$-alkyl, $C_3$-$C_6$-cycloalkyl, 3- to 6-membered saturated, partially unsaturated or maximally unsaturated heterocyclyl containing 1, 2, 3 or 4 heteroatoms or heteroatom groups selected from the group consisting of N, O, NO and $SO_2$ as ring members, $C_6$-$C_{10}$-aryl and $Si(R^{16})_3$, wherein the above $C_3$-$C_6$-cycloalkyl, 3- to 6-membered heterocyclyl and $C_6$-$C_{10}$-aryl groups are optionally substituted with 1, 2 or 3 substituents independently selected from the group consisting of $C_1$-$C_6$-alkyl, $C_1$-$C_6$-alkoxy and trifluoromethyl;

$R^{11}$, $R^{12}$, $R^{13}$, $R^{14}$, $R^{15}$ are each independently selected from the group consisting of hydrogen, halogen, $C_1$-$C_6$-alkyl, trifluoromethyl, $C_1$-$C_6$-alkoxy, $C_3$-$C_{10}$-cycloalkyl, 5- to 11-membered saturated, partially unsaturated or maximally unsaturated heterocyclyl containing 1, 2, 3 or 4 heteroatoms or heteroatom groups selected from the group consisting of N, O, NO and $SO_2$ as ring members, $C_6$-$C_{10}$-aryl, $NR^{16}R^{17}$, —Si$(R^{16})_3$ and —$SR^{16}$, wherein the above $C_3$-$C_{10}$-cycloalkyl, 5- to 11-membered heterocyclyl and $C_6$-$C_{10}$-aryl groups are optionally substituted with 1, 2 or 3 substituents independently selected from the group consisting of $C_1$-$C_6$-alkyl, $C_1$-$C_6$-alkoxy and trifluoromethyl;
or any two adjacent instances of $R^{11}$, $R^{12}$, $R^{13}$, $R^{14}$, $R^{15}$, together with the carbon atoms to which they are bound, form a five- or six-membered partially unsaturated or maximally unsaturated carbocyclic or heterocyclic ring, where the heterocyclic ring contains 1, 2, 3 or 4 heteroatoms or heteroatom groups selected from N, O, NO and $SO_2$ as ring members; where the carbocyclic or heterocyclic ring may carry one or more substituents selected from the group consisting of trifluoromethyl, $C_1$-$C_6$-alkyl, $C_1$-$C_6$-alkoxy, $C_3$-$C_{10}$-cycloalkyl, $C_6$-$C_{10}$-aryl, 5- to 11-membered saturated, partially unsaturated or maximally unsaturated heterocyclyl containing 1, 2, 3 or 4 heteroatoms or heteroatom groups selected from the group consisting of N, O, NO and $SO_2$ as ring members, and $NR^{16}R^{17}$, wherein the above $C_3$-$C_{10}$-cycloalkyl, 5- to 11-membered heterocyclyl and $C_6$-$C_{10}$-aryl groups are optionally substituted with 1, 2 or 3 substituents independently selected from the group consisting of $C_1$-$C_6$-alkyl, $C_1$-$C_6$-alkoxy and trifluoromethyl;

$R^{16}$, $R^{17}$ are each independently selected from the group consisting of hydrogen, trifluoromethyl, $C_1$-$C_6$-alkyl, $C_3$-$C_{10}$-cycloalkyl, saturated, partially unsaturated or maximally unsaturated 5- to 11-membered heterocyclyl containing 1, 2, 3 or 4 heteroatoms or heteroatom groups selected from the group consisting of N, O, NO and $SO_2$ as ring members, $C_6$-$C_{10}$-aryl, wherein the above $C_3$-$C_{10}$-cycloalkyl, 5- to 11-membered heterocyclyl and $C_6$-$C_{10}$-aryl groups are optionally substituted with 1, 2 or 3 substituents independently selected from the group consisting of halogen, $C_1$-$C_6$-alkyl, $C_1$-$C_6$-alkoxy and trifluoromethyl;

in a solvent mixture of water, a non-polar organic solvent and a polar aprotic co-solvent, with an organoboron compound of the formula IV

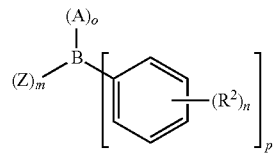

(IV)

wherein $R^2$ and n are as defined above and the compound of formula IV is selected from the group consisting of
(i) boronic acids with o=0, m=2; p=1 and Z=hydroxy, or their trimers;
(ii) boronic acid derivates with o=0, m=2; p=1 and Z=halogen; $C_1$-$C_4$-alkyl, $C_1$-$C_6$-alkoxy, $C_6$-$C_{10}$-aryl or $C_6$-$C_{10}$-aryloxy;
(iii) borinic acids or borinic acid derivatives with o=0, m=1; p=2 and Z=hydroxy, halogen, $C_1$-$C_4$-alkyl, $C_1$-$C_6$-alkoxy, $C_6$-$C_{10}$-aryl or $C_6$-$C_{10}$-aryloxy;
(iv) mixed borinic acids or borinic acid derivatives with o=1, m=1; p=1, A=$C_1$-$C_4$-alkyl and Z=hydroxy, halogen, $C_1$-$C_4$-alkyl, $C_1$-$C_6$-alkoxy, $C_6$-$C_{10}$-aryl or $C_6$-$C_{10}$-aryloxy;
(v) cyclic boronic esters with o=0, m=2 and p=1, wherein the two Z groups form together a bridging group —O—$(CH_2)_q$—O—, wherein q is 2 or 3, so that the two Z groups, together with the boron atom to which they are attached, form a 5- or 6-membered ring, where each $CH_2$ group is independently optionally substituted by one or two $C_1$-$C_4$-alkyl groups;
(vi) boronates with o=0, m=3, p=1 and Z=hydroxy, halogen, $C_1$-$C_4$-alkyl, $C_1$-$C_6$-alkoxy, $C_6$-$C_{10}$-aryl or $C_6$-$C_{10}$-aryloxy, and accompanied by a cation which compensates the negative charge of the boronate anion;
(vii) triarylboranes with o=0, m=0 and p=3;
(viii) tetraarylborates with o=0, m=0 and p=4, and accompanied by a cation which compensates the negative charge of the borate anion.

2. The process of claim 1, wherein $R^1$ is nitro.

3. The process of claim 1, wherein $R^2$ is fluorine or chlorine, and n is 1, 2 or 3.

4. The process of claim 1, wherein $R^3$ is hydrogen or fluorine.

5. The process of claim 1, wherein $R^1$ and $R^3$ are in para positions to one another.

6. The process of claim 1, wherein the biphenyl I is 4-chloro-2'-nitro-biphenyl, 3,4-dichloro-2'-nitro-biphenyl, 3,4-difluoro-2'-nitro-biphenyl, 3,4,5-trifluoro-2'-nitro-biphenyl, 3-chloro-4,5-difluoro-2'-nitro-biphenyl, 3,4-dichloro-5'-fluoro-2'-nitro-biphenyl, 3,5-dichloro-4-fluoro-2'-nitro-biphenyl, 4'-chloro-biphenyl-2-ylamine, 3',4'-dichloro-biphenyl-2-ylamine, 3',4'-difluoro-biphenyl-2-ylamine, 3',4',5'-trifluoro-biphenyl-2-ylamine, 3'-chloro-4',5'-difluoro-biphenyl-2-ylamine, 3',4'-dichloro-5-fluoro-biphenyl-2-ylamine or 3',5'-dichloro-4'-fluoro-biphenyl-2-ylamine.

7. The process of claim 1, wherein the phosphorus ligand III is a compound of formula IIIa

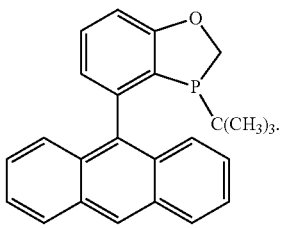

(IIIa)

8. The process of claim 1, wherein the palladium source is a palladium(II) salt or a palladium(0) complex.

9. The process of claim 1, wherein the palladium source, calculated on the basis of the Pd content, is used in an amount of from 0.0001 mol % to 0.5 mol %, relative to 1 mol of compound II or compound IV, if these are used in equimolar amounts, or, if compounds II and IV are not used in equimolar amounts, relative to 1 mol of that compound II or IV which is not used in excess.

10. The process of claim 9, wherein the palladium source, calculated on the basis of the Pd content, is used in an amount of from 0.0001 mol % to 0.01 mol %, relative to 1 mol of compound II or of compound IV, if these are used in equimolar amounts, or, if compounds II and IV are not used in equimolar amounts, relative to 1 mol of that compound II or IV which is not used in excess.

11. The process of claim 1, wherein the organoboron compound IV is a phenylboronic acid IVa or a diphenylborinic acid IVc

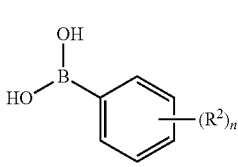

(IVa)

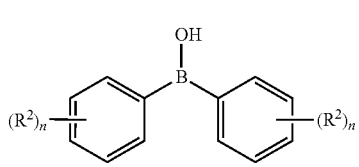

(IVc)

or a mixture of IVa and IVc, in which $R^2$ and n are each as defined in claim 1.

12. The process of claim 1, wherein the reaction is performed at a temperature of from 50 to 140° C.

13. The process of claim 1, wherein the non-polar organic solvent is selected from the group consisting of aliphatic hydrocarbons, cycloaliphatic hydrocarbons, chlorinated aliphatic hydrocarbons, aromatic hydrocarbons, open-chained ethers and mixtures thereof; and the polar aprotic co-solvent is selected from the group consisting of amides, sulfoxides, lactams, cyclic ethers, ketones, nitriles, lactones, nitro compounds, ureas, sulfones, carbonic acid esters and mixtures thereof.

14. The process of claim 13, wherein the non-polar organic solvent is an aromatic hydrocarbon.

15. The process of claim 13, wherein the polar aprotic co-solvent is a cyclic ether.

16. The process of claim 1, where in the solvent mixture water, the non-polar organic solvent and the polar aprotic co-solvent are contained in following amounts:
water: 0.5 to 20% by weight, based on the total weight of the solvent mixture;
non-polar organic solvent: 20 to 99% by weight, based on the total weight of the solvent mixture; and
polar aprotic co-solvent: 1 to 60% by weight, based on the total weight of the solvent mixture;
where the amounts of water, non-polar organic solvent and polar aprotic co-solvent add to 100% by weight.

17. The process of claim 16, wherein the solvent mixture water, the non-polar organic solvent and the polar aprotic co-solvent are contained in following amounts:
water: 1 to 15% by weight, based on the total weight of the solvent mixture;
non-polar organic solvent: 60 to 96% by weight, based on the total weight of the solvent mixture; and
polar aprotic co-solvent: 3 to 25% by weight, based on the total weight of the solvent mixture;
wherein the amounts of water, non-polar organic solvent and polar aprotic co-solvent add to 100% by weight.

18. The process of claim 1, wherein the base is selected from inorganic bases.

19. The process claim 18, wherein the base is potassium carbonate.

20. The process of claim 1, wherein the substituted biphenyls obtained, wherein $R^1$ nitro, amino, —N(H)PG, —NH—CO—R' or —N=CR'R", are subsequently converted to carboxamides of the formula V

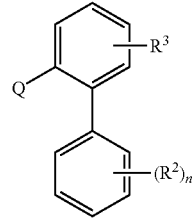

(V)

where Q is $Q^1$, $Q^2$ or $Q^3$, where $Q^1$, $Q^2$ and $Q^3$ are as defined in claim 1, and $R^2$, $R^3$ and n are as defined in any of claim 1,
by following reaction:
in case that $R^1$ is an amino group: subjecting the compound (I) wherein $R^1$ is an amino group to an N-acylation with an acyl precursor of one of the radicals $Q^1$, $Q^2$ or $Q^3$ to obtain a compound of formula (V);
in case that $R^1$ is a nitro group: reducing the compound (I) wherein $R^1$ is a nitro group to a compound (I) wherein $R^1$ is an amino group; and subjecting the compound (I) wherein $R^1$ is an amino group to an N-acylation with an acyl precursor of one of the radicals Q¹, Q² or Q³ to obtain a compound of formula (V);

in case that R¹ is a —N(H)PG, —NH—CO—R' or —N=CR'R" group: subjecting the compound (I) wherein R¹ is a —N(H)PG, —NH—CO—R' or —N=CR'R" group to a deprotection reaction to a compound (I) wherein R¹ is an amino group; and subjecting the com-pound (I) wherein R¹ is an amino group to an N-acylation with an acyl precursor of one of the radicals Q¹, Q² or Q³ to obtain a compound of formula (V);

where the acyl precursor of one of the radicals Q¹, Q² or Q³ is a compound $Q^{11}$, $Q^{22}$ or $Q^{33}$

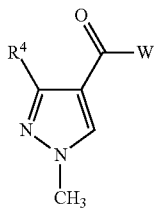

(Q¹¹)

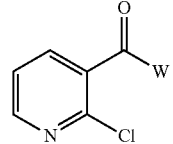

(Q²²)

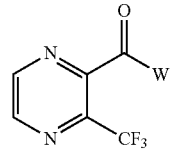

(Q³³)

wherein R⁴ is as defined in claim 1 and W is —OH, a halide, —OR$^A$, or —O—C(O)—R$^B$, where the compound $Q^{11}$, $Q^{22}$ or $Q^{33}$ wherein W is —OR$^A$ is an ester of a $C_1$-$C_4$-alkanol R$^A$OH in which R$^A$ is $C_1$-$C_4$-alkyl, of a $C_2$-$C_6$-polyol, of p-nitrophenol, N-hydroxybenzotriazole, N-hydroxysuccinimide or pentafluorophenol; and the compound $Q^{11}$, $Q^{22}$ or $Q^{33}$ wherein W is O—C(O)—R$^B$ is a symmetric anhydride or is an asymmetric anhydride with chloroformic acid or chloroacetic acid.

\* \* \* \* \*